(12) United States Patent
Urch et al.

(10) Patent No.: US 6,177,442 B1
(45) Date of Patent: Jan. 23, 2001

(54) BICYCLIC AMINE DERIVATIVES

(75) Inventors: Christopher John Urch; Terence Lewis; Raymond Leo Sunley; Roger Salmon; Christopher Richard Ayles Godfrey; Christopher Ian Brightwell; Matthew Brian Hotson, all of Bracknell (GB)

(73) Assignee: Zeneca Limited (GB)

( * ) Notice: Under 35 U.S.C. 154(b), the term of this patent shall be extended for 0 days.

(21) Appl. No.: 09/357,750

(22) Filed: Jul. 21, 1999

Related U.S. Application Data

(62) Division of application No. 08/969,978, filed on Nov. 13, 1997, now Pat. No. 5,968,947.

(30) Foreign Application Priority Data

| Nov. 26, 1996 | (GB) | 9624516 |
|---|---|---|
| Nov. 26, 1996 | (GB) | 9624611 |
| Nov. 26, 1996 | (GB) | 9624614 |

(51) Int. Cl.$^7$ ........................ A61K 31/46; C07D 451/02; A01N 43/90
(52) U.S. Cl. .................. 514/299; 546/112; 546/124; 546/125; 546/183; 504/246; 504/235; 544/405; 514/254; 514/304; 424/405
(58) Field of Search .................. 514/299, 254, 514/304; 424/405; 546/112, 124, 125, 183; 544/405; 504/246, 235

(56) References Cited

U.S. PATENT DOCUMENTS

| 3,120,537 | 2/1964 | Archer et al. ................. 260/291 |
|---|---|---|
| 3,133,073 | 5/1964 | Archer ........................... 260/292 |
| 3,308,131 | 3/1967 | McKusick ....................... 260/294 |
| 3,501,461 | 3/1970 | Newallis et al. ................ 260/239 |
| 3,546,232 | 12/1970 | Kaiser et al. ................. 260/292 |
| 3,556,943 | 1/1971 | Fonken et al. .................. 195/51 |
| 3,657,257 | 4/1972 | Helsley et al. ................ 260/292 |
| 4,180,669 | 12/1979 | Winn .............................. 546/240 |
| 4,393,069 | 7/1983 | Langbein et al. ............... 424/265 |
| 4,590,270 | 5/1986 | Kompis et al. .................. 544/320 |
| 4,774,249 | 9/1988 | Kompis et al. .................. 514/272 |
| 5,491,148 | 2/1996 | Berger et al. ................. 514/305 |
| 5,859,024 | * 1/1999 | Hotson et al. ................. 514/299 |

FOREIGN PATENT DOCUMENTS

| 27 49 584 | 5/1978 | (DE) . |
|---|---|---|
| 0 031 219 | 7/1981 | (EP) . |
| 0 216 625 | 4/1987 | (EP) . |
| 0 307 142 | 3/1989 | (EP) . |
| 0 315 390 | 5/1989 | (EP) . |
| 0 398 578 | 11/1990 | (EP) . |
| 0 498 331 | 8/1992 | (EP) . |
| 0 518 805 | 12/1992 | (EP) . |
| 2 548 666 | 1/1985 | (FR) . |
| 1 061 472 | 3/1967 | (GB) . |
| 1 304 649 | 1/1973 | (GB) . |
| 91/17156 | 11/1991 | (WO) . |
| 92/01688 | 2/1992 | (WO) . |
| 93/00313 | 1/1993 | (WO) . |
| 93/14636 | 8/1993 | (WO) . |

(List continued on next page.)

OTHER PUBLICATIONS

Archer, S., et al., J. Am. Chem. Soc., "The Action of Nucleophilic Agents on 3 α–Chlorotropane," vol. 80, 1958, pp. 4677–4681.

(List continued on next page.)

* cited by examiner

Primary Examiner—Charanjit S. Aulakh
(74) Attorney, Agent, or Firm—Liza D. Hohenschutz

(57) ABSTRACT

The invention provides a compound of formula (I):

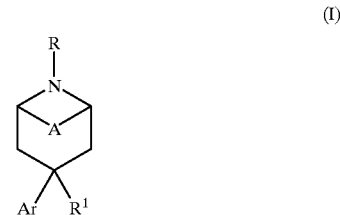

wherein A represents a bidentate group of formula —CH$_2$—X—CH$_2$— (wherein X is methylene, sulfur or oxygen), X'C=CY or X'WC—CYZ (wherein X', W, Y and Z are independently hydrogen, hydroxy, acyloxy, alkoxy, alkylsilyloxy, cyano or halogen, or X' and W or Y and Z together with the carbon to which they are attached form a carbonyl group), provided that A is not CH$_2$—CH$_2$; Ar is an optionally substituted phenyl or 5- or 6-membered heterocyclic ring system containing from 1 to 3 heteroatoms individually selected from nitrogen, oxygen and sulfur atoms, and at least one unsaturation (double bond) between adjacent atoms in the ring, said heterocyclic ring being optionally fused to a benzene ring; aryl, heteroaryl, aralkyl, heteroarylalkyl, alkenyl, aralkenyl, alkynyl, alkoxycarbonyl, alkanesulfonyl, arenesulfonyl, alkanyloxycarbonyl, aralkyloxycarbonyl, aryloxycarbonyl, heterocyclylalkyl, carbamyl, dithiocarboxyl moieties of R, R$^3$ and R$^4$ comprise from 1 to 15 carbon atoms, and are optionally substituted with one or more substituents selected from, halogen, cyano, carboxyl, carboxylic acyl, carbamyl, alkoxycarbonyl, alkoxy, alkylenedioxy, hydroxy, nitro, haloalkyl, alkyl, amino, acylamino, imidate and phosphonato groups; or an acid addition salt, quaternary ammonium salt or N-oxide derived therefrom; an insecticidal, acaricidal or nematicidal composition comprising a compound of formula (I) and a suitable carrier or diluent therefor; a method of combating and controlling insect, acarine or nematode pests at a locus which comprises treating the pests or the locus of the pests with an effective amount of a compound of formula (I) or a composition as hereinbefore described.

9 Claims, No Drawings

FOREIGN PATENT DOCUMENTS

| | | |
|---|---|---|
| 93/25527 | 12/1993 | (WO). |
| 95/03306 | 2/1995 | (WO). |
| 96/08968 | 3/1996 | (WO). |
| 96/36637 | 11/1996 | (WO). |
| 96/37494 | 11/1996 | (WO). |
| 97/13770 | 4/1997 | (WO). |
| 97/43286 | 11/1997 | (WO). |

OTHER PUBLICATIONS

Bell, M.R., et al., J. Am. Chem. Soc., "Ethyl 3α–Phenyltropane–3β–carboxylate and Related Compounds," vol. 82, No. 7–9, 1960, pp. 4638–4641.

Cignarella, G., et al., J. Am. Chem. Soc., "A New Synthesis of Tropane Derivatives," vol. 83, No. 10–12, 1961, pp. 4999–5003.

Daum, S. J., et al., J. Med. Chem., "Analgesic Activity of the Epimeric Tropane Analogs of Meperidine. A Physical and Pharmacological Study," vol. 18, No. 5, 1975, pp. 496–501.

Gutkowska, B., et al., Acta Polon. Pharm., "Syntezy Niektorych Pochodnych 8–Alkilo–8–Aza–Bicyklo[3.2.1] Oktan–3–Onu," vol. 38, No. 4, 1981, pp. 411–415.

Lowe, J. A., et al., J. Med. Chem., "Aza–Tricyclic Substance P Antagonists," vol. 37, No. 18, 1994, pp. 2831.

Maag, H., et al., Helvetica Chimica Acta, "94. 5–(N–Arylnortropan–3–yl)–and 5–(N–Arylpiperidin–4–yl)–2,4–diaminopyrimidines. Novel Inhibitors of Dihydrofolate Reductase," vol. 69, No. 4, 1986, pp. 887–897.

Repke, D. B., et al., J. Org. Chem., "Abbreviated Ibogaine Congeners. Synthesis and Reactions of Tropan–3–yl–2–and –3–indoles. Investigation of an Unusual Isomerization of 2–Substituted Indoles Using Computational and Spectroscopic Techniques," vol. 59, No. 8, 1994, pp. 2164–2171.

Zirkle, C. L., et al., J. Org. Chem., "The Isomeric 3–Oxa–and 3–Thiagranatanin–7–ols and Their Derivatives; Reduction of Bicyclic Amino Ketones Related to Tropinone," vol. 26, 1961, pp. 395–407.

BICYCLIC AMINE DERIVATIVES

This is a divisional application of application Ser. No. 08/969,978 filed on Nov. 13, 1997, now U.S. Pat. No. 5,968,947.

This invention relates to novel bicyclic amine derivatives, to processes for preparing them, to insecticidal compositions comprising them and to methods of using them to combat and control insect pests.

The present invention provides a compound of formula (I):

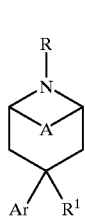

(I)

wherein A represents a bidentate group of formula —$CH_2$—X—$CH_2$— (wherein X is methylene, sulfur or oxygen), X'C=CY or X'WC—CYZ (wherein X', W, Y and Z are independently hydrogen, hydroxy, acyloxy, alkoxy, alkylsilyloxy, cyano or halogen, or X' and W or Y and Z together with the carbon to which they are attached form a carbonyl group), provided that A is not $CH_2$—$CH_2$; Ar is an optionally substituted phenyl or 5- or 6-membered heterocyclic ring system containing from 1 to 3 heteroatoms individually selected from nitrogen, oxygen and sulfur atoms, and at least one unsaturation (double bond) between adjacent atoms in the ring, said heterocyclic ring being optionally fused to a benzene ring, wherein the substutuents, if present, are selected from halogen atoms, cyano, alkyl, alkenyl, alkynyl, alkoxy, haloalkyl, haloalkenyl, alkylthio and alkyl amino groups, any of which groups contain up to six carbon atoms; R is hydrogen or cyano or a group selected from alkyl, aryl, heteroaryl, aralkyl, heteroarylalkyl, alkenyl, aralkenyl, alkynyl, alkoxycarbonyl, alkanesulfonyl, arenesulfonyl, alkenyloxycarbonyl, aralkyloxycarbonyl, aryloxycarbonyl, heterocyclylalkyl, carbamyl, dithiocarboxyl or X"$R^3$ (where X" represents oxygen or a group $NR^4$), provided that when R is alkenyl, aralkenyl or alkynyl said group does not have an unsaturated carbon atom bonding directly to the ring nitrogen of formula (I); $R^1$ is hydrogen, cyano, hydroxy, alkyl, alkoxy, amino, nitro, isocyanato, acylamino, hydroxyalkyl, optionally substituted heteroaryl, alkoxyalkyl, haloalkyl, halohydroxyalkyl, aralkyloxyalkyl, acyloxyalkyl, amidoximido, sulfonyloxyalkyl, aminoalkyl, alkoxycarbonylamino, acylaminoalkyl, cyanoalkyl, imino, formyl, acyl or carboxylic acid or an ester or amide thereof, or alkenyl or alkynyl either of which is optionally substituted by halogen, alkoxy, cycloalkyl, optionally substituted aryl, optionally substituted heteroaryl or cyano; $R^3$ and $R^4$ are, independently, hydrogen, alkyl, aryl, heteroaryl, aralkyl, heteroarylalkyl, alkenyl, aralkenyl, alkynyl, heterocyclylalkyl, alkoxycarbonyl or carboxylic acyl; alkyl moieties of R, $R^3$ and $R^4$ comprise from 1 to 15 carbon atoms, and are optionally substituted with one or more substituents selected from, halogen, cyano, carboxyl, carboxylic acyl, carbamyl, alkoxycarbonyl, alkoxy, alkylenedioxy, hydroxy, nitro, amino, acylamino, imidate and phosphonato groups; aryl, heteroaryl, aralkyl, heteroarylalkyl, alkenyl, aralkenyl, alkynyl, alkoxycarbonyl, alkanesulfonyl, arenesulfonyl, alkanyloxycarbonyl, aralkyloxycarbonyl, aryloxycarbonyl, heterocyclylalkyl, carbamyl, dithiocarboxyl moieties of R, $R^3$ and $R^4$ comprise from 1 to 15 carbon atoms, and are optionally substituted with one or more substituents selected from, halogen, cyano, carboxyl, carboxylic acyl, carbamyl, alkoxycarbonyl, alkoxy, alkylenedioxy, hydroxy, nitro, haloalkyl, alkyl, amino, acylamino, imidate and phosphonato groups; or an acid addition salt, quaternary ammonium salt or N-oxide derived therefrom.

It will be appreciated that the bicyclic amine compounds of formula (I) are capable of existing in more than one isomeric form since groups may be positioned in either an exo or endo relationship, and the present invention embraces within its scope both exo and endo forms and mixtures thereof in all proportions and also any further isomeric variants arising from cis and trans substitution patterns or chiral centres.

Examples of 5- and 6-membered heterocyclic ring systems represented by Ar include those based on pyridine, pyrazine, pyridazine, pirimidine, pyrrole, pyrazole, imidazole, 1,2,3- and 1,2,4-triazoles, furan, thiophene, oxazole, isoxazole, thiazole, isothiazole, 1,2,3- and 1,3,4-oxadiazoles, and 1,2,3- and 1,3,4-thiadiazoles, and partially reduced containing one double bond derived from these, as well as those based on oxathiole, dioxole, and dithiole rings containing one double bond. Preferably Ar represents a halo-substituted phenyl, pyridyl or diazinyl group.

When Ar is a 5- or 6- membered hererocyclic ring fused to a benzene ring it is preferably benzoxazole, indole, benzofuran, benzothiophen or benzimidazole.

Halogen includes fluorine, chlorine, bromine and iodine.

Alkyl moieties preferably contain from 1 to 6, more preferably from 1 to 4, carbon atoms. They can be in the form of straight or branched chains, for example methyl, ethyl, n- or iso-propyl, or n-, sec-, iso- or tert-butyl.

Haloalkyl is preferably $C_{1-6}$ haloalkyl, especially fluoroalkyl (for example trifluoromethyl, 2,2,2-trifluoroethyl or 2,2-difluoroethyl) or chloroalkyl. For R haloalkyl is preferably $C_{2-6}$ haloalkyl wherein there is no halogen on the α-carbon (for example it is 2,2,2-trifluoroethyl or 2,2-difluoroethyl).

Alkenyl and alkynyl moieties of $R^1$ and substituents of Ar preferably contain from 2 to 6, more preferably from 2 to 4, carbon atoms. They can be in the form of straight or branched chains, and, where appropriate, the alkenyl moieties can be of either (E)- or (Z)-configuration. Examples are vinyl, allyl and propargyl.

Aryl includes naphthyl but is preferably phenyl.

Heteroaryl includes 5- and 6-membered aromatic rings containing one, two, three or four heteroatoms selected from the list comprising oxygen, sulphur and nitrogen and can be fused to benzenoid ring systems. Examples of heteroaryl are pyridinyl, pyrimidinyl, pyridazinyl, pyrazinyl, triazinyl (1,2, 3-, 1,2,4- and 1,3,5-), furyl, thienyl, pyrrolyl, pyrazolyl, imidazolyl, triazolyl (1,2,3- and 1,2,4-), tetrazolyl, oxazolyl, isoxazolyl, thiazolyl, isothiazolyl, oxadiazolyl, thiadiazolyl, quinolinyl, isoquinolinyl, cinnolinyl, quinazolinyl, quinoxalinyl, indolinyl, isoindolinyl, benzofuranyl, benzothienyl and benzimidazolinyl.

The heterocyclyl part of heterocyclylalkyl is a ring containing one or two heteroatoms selected from the list comprising oxygen, sulphur and nitrogen. Examples are piperidine, piperazine, pyrrolidine, tetrahydrofuran, morpholine, thietane, pyridine or thiazole.

The alkylenedioxy group is a substituent for a ring and is especially $C_{1-4}$ alkylenedioxy. Alkylenedioxy groups are optionally substituted with halogen (especially flourine) and are, for example, methylenedioxy (OCH$_2$O) or difluoromethylenedioxy (OCF$_2$O).

Suitable acid addition salts include those with an inorganic acid such as hydrochloric, hydrobromic, sulfuric, nitric and phosphoric acids, or an organic carboxylic acid such as oxalic, tartaric, lactic, butyric, toluic, hexanoic and phthalic acids, or sulphonic acids such as methane, benzene and toluene sulphonic acids. Other examples of organic carboxylic acids include haloacids such as trifluoroacetic acid.

In one particular aspect the present invention provides a compound of formula (I), wherein A represents a bidentate group of formula —CH$_2$—X—CH$_2$— (wherein X is methylene, sulfur or oxygen), X'C=CY or X'WC—CYZ (wherein X', W, Y and Z are independently hydrogen, hydroxy, acyloxy (especially $C_{1-4}$ alkylcarbonyl), alkoxy (especially $C_{1-4}$ alkoxy), alkylsilyloxy (especially $C_{1-4}$ alkylsilyloxy), cyano or halogen, or X' and W or Y and Z together with the carbon to which they are attached form a carbonyl group), provided that A is not CH$_2$—CH$_2$; Ar is optionally substituted phenyl or optionally substituted 5- or 6-membered heterocyclic ring containing from 1 to 3 heteroatoms individually selected from nitrogen, oxygen and sulfur atoms, and at least one unsaturation (double bond) between adjacent atoms in the ring, said heterocyclic ring being optionally fused to a benzene ring, wherein the substutuents, if present, are selected from halogen atoms, cyano, alkyl (especially $C_{1-4}$ alkyl), alkenyl (especially $C_{2-4}$ alkenyl), alkynyl (especially $C_{2-4}$ alkynyl), alkoxy (especially $C_{1-4}$ alkoxy), haloalkyl (especially $C_{1-4}$ haloalkyl), haloalkenyl (especially $C_{2-4}$ haloalkenyl), alkylthio (especially $C_{1-4}$ alkylthio), and alkyl amino (especially mono- or di- ($C_{1-4}$ alkyl)amino, such as mono- or di- ($C_{1-3}$ alkyl)amino) groups; R represents hydrogen or cyano or a group selected from alkyl (especially $C_{1-4}$ alkyl), aryl (especially phenyl), heteroaryl (especially pyridinyl or pyrimidinyl), aralkyl (especially aryl($C_{1-4}$)alkyl, such as phenyl($C_{1-4}$) alkyl), heteroarylalkyl (especially heteroaryl ($C_{1-4}$)alkyl, such as pyridinyl($C_{1-4}$)alkyl or pyrimidinyl($C_{1-4}$)alkyl), alkenyl (especially $C_{3-4}$ alkenyl), aralkenyl (especially aryl($C_{3-4}$)alkenyl, such as phenyl($C_{3-4}$)alkenyl), alkynyl (especially $C_{3-4}$ alkynyl), alkoxycarbonyl (especially $C_{1-4}$ alkoxycarbonyl), alkanesulfonyl (especially $C_{1-4}$ alkylsulfonyl), arenesulfonyl (especially phenylsulfonyl), alkenyloxycarbonyl (especially $C_{3-4}$ alkenyloxycarbonyl), aralkyloxycarbonyl (especially phenyl ($C_{1-4}$)alkoxycarbonyl), aryloxycarbonyl (especially phenoxycarbonyl), heterocyclylalkyl (especially heterocyclyl($C_{1-4}$)alkyl, such as piperidinyl($C_{1-4}$)alkyl), carbamyl (H$_2$NC(O)), dithiocarboxyl or X"R$^3$ (where X" represents oxygen or a group NR$^4$), provided that when R is alkenyl, aralkenyl or alkynyl said group does not have an unsaturated carbon atom bonding directly to the ring nitrogen of formula (I); R$^1$ is hydrogen, cyano, hydroxy, alkyl (especially $C_{1-4}$ alkyl), alkoxy (especially $C_{1-4}$ alkoxy), amino (especially unsubstituted, mono- or di-($C_{1-4}$) alkylamino or amino substituted with a formyl group), nitro, isocyanato, acylamino (especially $C_{1-4}$ alkylcarbonylamino or phenylcarbonylamino), hydroxyalkyl (especially monohydroxy($C_{1-4}$)alkyl), optionally substituted heteroaryl (especially tetrazole, oxadiazole, pyridinyl or pyrimidinyl optionally substituted by halogen, $C_{1-4}$ alkyl, $C_{1-4}$ haloalkyl, $C_{1-4}$ alkoxy or $C_{1-4}$ haloalkoxy), alkoxyalkyl (especially $C_{1-4}$ alkoxy($C_{1-4}$)alkyl), haloalkyl (especially $C_{1-4}$ haloalkyl), halohydroxyalkyl (especially $C_{1-4}$ halohydroxyalkyl, such as 2-hydroxy-1,1-difluoroethyl), aralkyloxyalkyl (especially phenyl($C_{1-4}$)alkoxy($C_{1-4}$)alkyl), acyloxyalkyl (especially $C_{1-4}$ alkylcarbonyloxy($C_{1-4}$)alkyl), amidoximido (C(NH$_2$)NOH), sulfonyloxyalkyl (especially sulfonyloxy($C_{1-4}$)alkyl), aminoalkyl (especially amino($C_{1-4}$)alkyl), alkoxycarbonylamino (especially $C_{1-4}$ alkoxycarbonylamino), acylaminoalkyl (especially $C_{1-4}$ alkylcarbonylamino($C_{1-4}$)alkyl or phenylcarbonylamino($C_{1-4}$)alkyl), cyanoalkyl (especially $C_{1-4}$ cyanoalkyl), imino (especially hydroxyimino (HON=CH) or $C_{1-4}$ alkoxyimino), formyl, acyl (especially $C_{1-4}$ alkylcarbonyl) or carboxylic acid or an ester (especially a $C_{1-4}$ alkyl ester) or amide (especially an unsubstituted or an N,N-di($C_{1-4}$) alkyl amide) thereof, or alkenyl (especially $C_{2-4}$ alkenyl) or alkynyl (especially $C_{2-4}$ alkynyl) either of which is optionally substituted by halogen, alkoxy (especially $C_{1-4}$ alkoxy), cycloalkyl (especially $C_{3-7}$ cycloalkyl, such as cyclopropyl or cyclohexyl), optionally substituted aryl (especially phenyl optionally substituted by halogen, $C_{1-4}$ alkyl, $C_{1-4}$ haloalkyl, $C_{1-4}$ alkoxy or $C_{1-4}$ haloalkoxy), optionally substituted heteroaryl (especially pyridinyl or pyrimidinyl optionally substituted by halogen, $C_{1-4}$ alkyl, $C_{1-4}$ haloalkyl, $C_{1-4}$ alkoxy or $C_{1-4}$ haloalkoxy) or cyano; R$^3$ and R$^4$ are, independently, hydrogen, alkyl (especially $C_{1-4}$ alkyl), aryl (especially phenyl), heteroaryl (especially pyridinyl or pyrimidinyl), aralkyl (especially aryl($C_{1-4}$)alkyl, such as phenyl($C_{1-4}$) alkyl), heteroarylalkyl (especially heteroaryl($C_{1-4}$)alkyl, such as pyridinyl($C_{1-4}$)alkyl or pyrimidinyl($C_{1-4}$)alkyl), alkenyl (especially $C_{2-4}$ alkenyl), aralkenyl (especially aryl($C_{2-4}$)alkenyl, such as phenyl($C_{2-4}$)alkenyl), alkynyl (especially $C_{2-4}$ alkynyl), heterocyclylalkyl (especially heterocyclyl($C_{1-4}$)alkyl, such as piperidinyl($C_{1-4}$)alkyl), alkoxycarbonyl (especially $C_{1-4}$ alkoxycarbonyl) or carboxylic acyl (especially $C_{1-4}$ alkylcarbonyloxy); alkyl moieties of R, R$^3$ and R$^4$ comprise from 1 to 15 carbon atoms, and are optionally substituted with one or more substituents selected from halogen, cyano, carboxyl (HOC(O)), carboxylic acyl (especially $C_{1-4}$ alkylcarbonyloxy), carbamyl (H$_2$NC(O)), alkoxycarbonyl (especially $C_{1-4}$ alkoxycarbonyl), alkoxy (especially $C_{1-4}$ alkoxy), alkylenedioxy (especially $C_{1-4}$ alkylenedioxy), hydroxy, nitro, amino, acylamino (especially $C_{1-4}$ alkylcarbonylamino), imidate ($C_{1-4}$ alkyl[C(O)NHC(O)]) and phosphonato (OP(OH)$_2$) groups; aryl, heteroaryl, aralkyl, heteroarylalkyl, alkenyl, aralkenyl, alkynyl, alkoxycarbonyl, alkanesulfonyl, arenesulfonyl, alkenyloxycarbonyl, aralkyloxycarbonyl, aryloxycarbonyl, heterocyclylalkyl, carbamyl, dithiocarboxyl moieties of R, R$^3$ and R$^4$ comprise from 1 to 15 carbon atoms, and are optionally substituted with one or more substituents selected from, halogen, cyano, carboxyl (HOC(O)), carboxylic acyl (especially $C_{1-4}$ alkylcarbonyloxy), carbamyl (H$_2$NC(O)), alkoxycarbonyl (especially $C_{1-4}$ alkoxycarbonyl), alkoxy (especially $C_{1-4}$ alkoxy), alkylenedioxy (especially $C_{1-4}$ alkylenedioxy), hydroxy, nitro, haloalkyl (especially $C_{1-4}$ haloalkyl), alkyl (especially $C_{1-4}$ alkyl), amino, acylamino (especially $C_{1-4}$ alkylcarbonylamino), imidate ($C_{1-4}$ alkyl[C(O)NHC(O)]) and phosphonato (OP(OH)$_2$) groups; or an acid addition salt, quaternary ammonium salt or N-oxide derived therefrom.

In another aspect the invention provides compounds having the general formula (Ia)

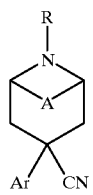

(Ia)

wherein A represents a bidentate group —CH$_2$—X—CH$_2$— where X is methylene, sulfur or oxygen; Ar represents an optionally substituted phenyl or 5- or 6-membered heterocyclic ring system containing from 1 to 3 heteroatoms individually selected from nitrogen, oxygen and sulfur atoms, and at least one unsaturation (double bond) between adjacent atoms in the ring, wherein the substutuents, if present, are selected from halogen atoms, alkyl, alkenyl, alkynyl, alkoxy, haloalkyl, haloalkenyl, alkylthio and alkyl amino groups, any of which groups contain up to six carbon, and wherein R represents hydrogen or cyano or a group selected from alkyl, aryl, heteroaryl, aralkyl, heteroarylalkyl, alkenyl, aralkenyl, alkynyl, alkoxycarbonyl, alkanesulfonyl, arenesulfonyl, alkanyloxycarbonyl, aralkyloxycarbonyl, aryloxycarbonyl, heterocyclylalkyl, carbamyl or dithiocarboxyl groups, said groups comprising from 1 to 15 carbon atoms, said groups being optionally substituted with one or more substituents selected from, halogen, cyano, carboxyl, carboxylic acyl, carbamyl, alkoxycarbonyl, alkoxy, alkylenedioxy, hydroxy, nitro, haloalkyl, alkyl, amino, acylamino, imidate and phosphonato groups; and acid addition salts and quaternary ammonium salts and N-oxides derived therefrom.

In a further aspect the invention provides compounds having the general formula (Ib)

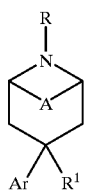

(Ib)

wherein A represents bidentate group —CH$_2$—X—CH$_2$— where X is methylene, sulfur or oxygen; Ar represents an optionally substituted phenyl or 5- or 6-membered heterocyclic ring system containing from 1 to 3 heteroatoms individually selected from nitrogen, oxygen and sulfur atoms, and at least one unsaturation (double bond) between adjacent atoms in the ring, wherein the substutuents, if present, are selected from halogen atoms, alkyl, alkenyl, alkynyl, alkoxy, haloalkyl, haloalkenyl, alkylthio and alkyl amino groups, any of which groups contain up to six carbon, and wherein R represents hydrogen or cyano or a group selected from alkyl, aryl, heteroaryl, aralkyl, heteroarylalkyl, alkenyl, aralkenyl, alkynyl, alkoxycarbonyl, alkanesulfonyl, arenesulfonyl, alkanyloxycarbonyl, aralkyloxycarbonyl, aryloxycarbonyl, heterocyclylalkyl, carbamyl or dithiocarboxyl groups, said groups comprising from 1 to 15 carbon atoms, said groups being optionally substituted with one or more substituents selected from, halogen, cyano, carboxyl, carboxylic acyl, carbamyl, alkoxycarbonyl, alkoxy, alkylenedioxy, hydroxy, nitro, haloalkyl, alkyl, amino, acylamino, imidate and phosphonato groups; $R^1$ represents hydroxy, or a group selected from alkoxy, amino, acylamino, hydroxyalkyl, alkoxyalkyl, haloalkyl, halohydroxyalkyl, aralkyloxyalkyl, acyloxyalkyl, sulfonyloxyalkyl, aminoalkyl, acylaminoalkyl, cyanoalkyl, formyl, acyl, carboxylic acid and esters and amides thereof, alkenyl or alkynyl optionally substituted by halogen, alkoxy, aryl, heteroaryl or cyano; and acid addition salts and quaternary ammonium salts and N-oxides derived therefrom.

In a still further aspect the invention provides compounds having the general formula (Ic) or (Id)

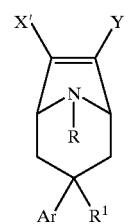

(Ic)

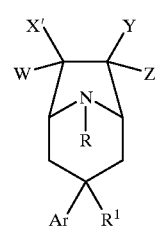

(Id)

wherein; Ar represents an optionally substituted phenyl or 5- or 6-membered heterocyclic ring system containing from 1 to 3 heteroatoms individually selected from nitrogen, oxygen and sulfur atoms, and at least one unsaturation (double bond) between adjacent atoms in the ring, wherein the substutuents, if present, are selected from halogen atoms, alkyl, alkenyl, alkynyl, alkoxy, haloalkyl, haloalkenyl, alkylthio and alkyl amino groups, any of which groups contain up to six carbon, wherein R represents hydrogen or cyano or a group selected from alkyl, aryl, heteroaryl, aralkyl, heteroarylalkyl, alkenyl, aralkenyl, alkynyl, alkoxycarbonyl, alkanesulfonyl, arenesulfonyl, alkanyloxycarbonyl, aralkyloxycarbonyl, aryloxycarbonyl, heterocyclylalkyl, carbamyl or dithiocarboxyl groups, said groups comprising from 1 to 15 carbon atoms, said groups being optionally substituted with one or more substituents selected from, halogen, cyano, carboxyl, carboxylic acyl, carbamyl, alkoxycarbonyl, alkoxy, alkylenedioxy, hydroxy, nitro, haloalkyl, alkyl, amino, acylamino, imidate and phosphonato groups; $R^1$ represents cyano; and W, X', Y and Z are selected from hydrogen, hydroxy, acyloxy, alkoxy, alkylsilyloxy and halogen; and acic addition salts and quaternary ammonium salts and N-oxides derived therefrom.

In a further aspect the present invention provides a compound of formula (I) wherein A is CH$_2$CH$_2$CH$_2$ or CH=CH.

In another aspect the present invention provides a compound of formula (I), wherein Ar is phenyl, pyridinyl, pyridazinyl or pyrazinyl, all being optionally substituted with halogen (especially fluorine, chlorine or bromine), $C_{1-4}$ alkyl (especially methyl), $C_{1-4}$ alkoxy (especially methoxy), $C_{2-4}$ alkenyl, $C_{2-4}$ alkynyl or cyano.

In a further aspect the present invention provides a compound of formula (I) wherein R is $C_{1-4}$ alkyl (optionally substituted with cyano, CO$_2$($C_{1-4}$ alkyl) or phenyl (itself optionally substituted with halogen, $C_{1-4}$ alkyl, $C_{1-4}$ alkoxy, $C_{1-4}$ haloalkyl or $C_{1-4}$ haloalkoxy)), $C_{2-4}$ haloalkyl (the α-carbon being unsubstituted), $C_{3-4}$ alkenyl or $C_{3-4}$ alkynyl; provided that when R is alkenyl or alkynyl said goup does not have an unsaturated carbon atom bonding directly to the ring nitrogen of formula (I).

In another aspect the present invention provides a compound of formula (I), wherein A is X'C=CY or $CH_2$—CYZ, wherein X' and Y are as defined above and Z is as defined above but is not hydrogen.

In a further aspect the present invention provides a compound of formula (I), wherein A is X'C=CY, wherein X' and Y are as defined above (but are both, preferably, hydrogen).

In another aspect the present invention provides a compound of formula (I), wherein A is $CH_2$—CYZ, wherein Y is hydrogen or halogen (especially fluorine or chlorine) and Z is halogen (especially fluorine).

In yet another aspect the present invention provides a compound of formula (I) wherein $R^1$ is cyano.

In a further aspect the present invention provides a compound of formula (I) wherein Ar is phenyl or pyridinyl, both being optionally substituted with halogen (especially fluorine, chlorine or bromine), cyano, $C_{1-4}$ alkyl, $C_{1-4}$ alkoxy or $C_{1-4}$ haloalkyl.

In a still further aspect the present invention provides a compound of formula (I) wherein R is hydrogen, $C_{1-4}$ alkyl, $C_{2-4}$ haloalkyl (the α-carbon being unsubstituted, especially $C_{2-4}$ fluoroalkyl), $C_{1-4}$ alkoxycarbonyl, $C_{1-4}$ cyanoalkyl, $C_{3-4}$ alkenyl or $C_{3-4}$ alkynyl, provided that when R is alkenyl or alkynyl said group does not have an unsaturated carbon atom bonding directly to the ring nitrogen of formula (I).

In yet another aspect the present invention provides a compound of formula (I) wherein Ar is pyridinyl optionally substituted with halogen (especially chlorine or bromine).

Specific compounds of formula (I) are set out in the Tables below.

TABLE 1

In Table I there are compounds of formula (I) wherein A is —$CH_2$—X—$CH_2$— and the groups Ar, R, $R^1$ and X are given for each compound, together with the molecular ion identified for each compound.

| Compound No. | Ar | R | $R^1$ | X | Molecular ion |
|---|---|---|---|---|---|
| 1 | pyrid-3-yl | allyl | CN | $CH_2$ | 267 |
| 2 | pyrid-3-yl | benzyl | CN | $CH_2$ | 317 |
| 3 | pyrid-3-yl | 3-chlorobenzyl | CN | $CH_2$ | 351 |
| 4 | 5-chloropyrid-3-yl | methyl | CN | O | 278 ($MH^+$) |
| 5 | 5-chloropyrid-3-yl | 2-methylpropyl | CN | $CH_2$ | 317 |
| 6 | 5-chloropyrid-3-yl | allyl | CN | $CH_2$ | 301 |
| 7 | 5-chloropyrid-3-yl | 3-chlorobenzyl | CN | $CH_2$ | 385 |
| 8 | 5-bromopyrid-3-yl | methyl | CN | $CH_2$ | 319 |
| 9 | 5-bromopyrid-3-yl | methyl | CN | O | 322 ($MH^+$) |
| 10 | 5-bromopyrid-3-yl | 2-methylpropyl | CN | $CH_2$ | 361 |
| 11 | 5-bromopyrid-3-yl | allyl | CN | $CH_2$ | 345 |
| 12 | 5-bromopyrid-3-yl | 2,2,2-trifluoroethyl | CN | $CH_2$ | 387 |
| 13 | 5-bromopyrid-3-yl | benzyl | CN | $CH_2$ | 395 |
| 14 | 5-bromopyrid-3-yl | 3-chlorobenzyl | CN | $CH_2$ | 431 |
| 15 | 6-chloropyrazin-2-yl | methyl | CN | $CH_2$ | 276 |
| 16 | 6-chloropyrazin-2-yl | 2-methylpropyl | CN | $CH_2$ | 318 |
| 17 | 6-chloropyrazin-2-yl | allyl | CN | $CH_2$ | 302 |
| 18 | 6-chloropyrazin-2-yl | benzyl | CN | $CH_2$ | 352 |
| 19 | 6-chloropyrazin-2-yl | 3-chlorobenzyl | CN | $CH_2$ | 386 |
| 20 | 3,5-dichlorophenyl | methyl | CN | $CH_2$ | 308 |
| 21 | 3,5-dichlorophenyl | 2-methylpropyl | CN | $CH_2$ | 350 |
| 22 | 3,5-dichlorophenyl | allyl | CN | $CH_2$ | 334 |
| 23 | 3,5-dichlorophenyl | 2,2,2-trifluoroethyl | CN | $CH_2$ | 376 |

TABLE 1-continued

In Table I there are compounds of formula (I) wherein A is —$CH_2$—X—$CH_2$— and the groups Ar, R, $R^1$ and X are given for each compound, together with the molecular ion identified for each compound.

| Compound No. | Ar | R | $R^1$ | X | Molecular ion |
|---|---|---|---|---|---|
| 24 | 3,5-dichlorophenyl | benzyl | CN | $CH_2$ | 384 |
| 25 | 3,5-dichlorophenyl | 3-chlorobenzyl | CN | $CH_2$ | 418 |
| 26 | 5-chloropyrid-3-yl | methyl | CN | $CH_2$ | |
| 27 | 5-chloropyrid-3-yl | benzyl | CN | $CH_2$ | |
| 28 | 5-chloropyrid-3-yl | 2,2,2-trifluoroethyl | CN | $CH_2$ | |
| 29 | 6-chloropyrazin-2-yl | 2,2,2-trifluoroethyl | CN | $CH_2$ | |
| 30 | 5-chloropyrid-3-yl | ($CH_2$=CHO)CO | CN | $CH_2$ | |
| 31 | 5-chloropyrid-3-yl | hydrogen | CN | $CH_2$ | |

TABLE II

In Table II there are compounds of formula (I) wherein A is —CH=CH— and the groups Ar and R are as given in the Table.

| Compound No. | Ar | R | $R^1$ |
|---|---|---|---|
| 1 | 5-bromopyrid-3-yl | methyl | CN |
| 2 | 5-chloropyrid-3-yl | methyl | CN |
| 3 | 6-chloropyrazin-2-yl | methyl | CN |
| 4 | pyrid-3-yl | methyl | CN |
| 5 | 5-chloropyrid-3-yl | benzyl | CN |
| 6 | 5-chloropyrid-3-yl | hydrogen | CN |
| 7 | 5-chloropyrid-3-yl | 2,2-difluoroethyl | CN |
| 8 | 5-bromopyrid-3-yl | $CH_2$=CHOC(O) | CN |
| 9 | 5-bromopyrid-3-yl | hydrogen | CN |
| 10 | 5-chloropyrid-3-yl | $CH_2$=CH$CH_2$ | CN |
| 11 | 5-bromopyrid-3-yl | 2,2,2-trifluoroethyl | CN |
| 12 | 5-bromopyrid-3-yl | 2-methylpentyl | CN |
| 13 | 5-chloropyrid-3-yl | 2,2,2-trifluoroethyl | CN |
| 14 | 5-chloropyrid-3-yl | 2-methylpropyl | CN |
| 15 | 5-chloropyrid-3-yl | ethoxycarbonyl | CN |
| 16 | 5-chloropyrid-3-yl | 3,3,3-trifluoropropyl | CN |
| 17 | 5-chloropyrid-3-yl | propargyl | CN |
| 18 | 5-chloropyrid-3-yl | but-2-yn-4-yl | CN |
| 19 | 5-chloropyrid-3-yl | 2-cyanoethyl | CN |
| 20 | 5-chloropyrid-3-yl | methyl propionyl | CN |
| 21 | 5-chloropyrid-3-yl | carbonyloxy methyl propion-2-yl | CN |
| 22 | 5-chloropyrid-3-yl | methoxy | CN |
| 23 | 5-chloropyrid-3-yl | benzoyloxy | CN |
| 24 | 5-chloropyrid-3-yl | hydroxy | CN |
| 25 | 6-methoxypyrazin-2-yl | methyl | CN |
| 26 | 5-bromopyridin-3-yl | $CH_2CHF_2$ | CN |
| 27 | 5-bromopyridin-3-yl | $CH_2C\equiv CH$ | CN |
| 28 | 5-bromopyridin-3-yl | $CH_2C\equiv CCH_3$ | CN |
| 29 | 5-bromopyridin-3-yl | $CH_2CO_2CH_3$ | CN |
| 30 | 5-bromopyridin-3-yl | $CH(CH_3)CO_2CH_3$ | CN |
| 31 | 5-bromopyridin-3-yl | $CO_2CH_3$ | CN |
| 32 | 5-bromopyridin-3-yl | $CH_2CH_2CN$ | CN |
| 33 | 5-bromopyridin-3-yl | $CH_2CN$ | CN |
| 34 | 5-bromopyridin-3-yl | $CH_2C_6H_5$ | CN |
| 35 | 5-bromopyridin-3-yl | $CH_2CH(CH_3)_2$ | CN |
| 36 | 5-bromopyridin-3-yl | $(CH_2)_2CF_3$ | CN |
| 37 | 5-chloropyridin-3-yl | $CH_2CH$=$CH_2$ | CN |
| 38 | 5-chloropyridin-3-yl | $CH_2CO_2CH_3$ | CN |
| 39 | 5-chloropyridin-3-yl | $CH(CH_3)CO_2CH_3$ | CN |
| 40 | 5-chloropyridin-3-yl | $CO_2CH_3$ | CN |
| 41 | 5-chloropyridin-3-yl | $CH_2CN$ | CN |
| 42 | 5-cyanopyridin-3-yl | $CH_2CHF_2$ | CN |
| 43 | 5-cyanopyridin-3-yl | $CH_2CF_3$ | CN |
| 44 | 5-cyanopyridin-3-yl | H | CN |
| 45 | 5-cyanopyridin-3-yl | $CH_2CH$=$CH_2$ | CN |
| 46 | 5-cyanopyridin-3-yl | $CH_2C\equiv CH$ | CN |
| 47 | 5-cyanopyridin-3-yl | $CH_2C\equiv CCH_3$ | CN |
| 48 | 5-cyanopyridin-3-yl | $CH_2CO_2CH_3$ | CN |
| 49 | 5-cyanopyridin-3-yl | $CH(CH_3)CO_2CH_3$ | CN |

TABLE II-continued

In Table II there are compounds of formula (I) wherein A is —CH=CH— and the groups Ar and R are as given in the Table.

| Compound No. | Ar | R | $R^1$ |
|---|---|---|---|
| 50 | 5-cyanopyridin-3-yl | $CO_2CH_3$ | CN |
| 51 | 5-cyanopyridin-3-yl | $CH_2CH_2CN$ | CN |
| 52 | 5-cyanopyridin-3-yl | $CH_2CN$ | CN |
| 53 | 5-cyanopyridin-3-yl | $CH_2C_6H_5$ | CN |
| 54 | 5-cyanopyridin-3-yl | $CH_2CH(CH_3)_2$ | CN |
| 55 | 5-cyanopyridin-3-yl | $CH_3$ | CN |
| 56 | 5-cyanopyridin-3-yl | $(CH_2)_2CF_3$ | CN |
| 57 | 5-methoxypyridin-3-yl | $CH_2CHF_2$ | CN |
| 58 | 5-methoxypyridin-3-yl | $CH_2CF_3$ | CN |
| 59 | 5-methoxypyridin-3-yl | H | CN |
| 60 | 5-methoxypyridin-3-yl | $CH_2CH=CH_2$ | CN |
| 61 | 5-methoxypyridin-3-yl | $CH_2C\equiv CH$ | CN |
| 62 | 5-methoxypyridin-3-yl | $CH_2C\equiv CCH_3$ | CN |
| 63 | 5-methoxypyridin-3-yl | $CH_2CO_2CH_3$ | CN |
| 64 | 5-methoxypyridin-3-yl | $CH(CH_3)CO_2CH_3$ | CN |
| 65 | 5-methoxypyridin-3-yl | $CO_2CH_3$ | CN |
| 66 | 5-methoxypyridin-3-yl | $CH_2CH_2CN$ | CN |
| 67 | 5-methoxypyridin-3-yl | $CH_2CN$ | CN |
| 68 | 5-methoxypyridin-3-yl | $CH_2C_6H_5$ | CN |
| 69 | 5-methoxypyridin-3-yl | $CH_2CH(CH_3)_2$ | CN |
| 70 | 5-methoxypyridin-3-yl | $CH_3$ | CN |
| 71 | 5-methoxypyridin-3-yl | $(CH_2)_2CF_3$ | CN |
| 72 | 5-acetylenylpyridin-3-yl | $CH_2CHF_2$ | CN |
| 73 | 5-acetylenylpyridin-3-yl | $CH_2CF_3$ | CN |
| 74 | 5-acetylenylpyridin-3-yl | H | CN |
| 75 | 5-acetylenylpyridin-3-yl | $CH_2CH=CH_2$ | CN |
| 76 | 5-acetylenylpyridin-3-yl | $CH_2C\equiv CH$ | CN |
| 77 | 5-acetylenylpyridin-3-yl | $CH_2C\equiv CCH_3$ | CN |
| 78 | 5-acetylenylpyridin-3-yl | $CH_2CO_2CH_3$ | CN |
| 79 | 5-acetylenylpyridin-3-yl | $CH(CH_3)CO_2CH_3$ | CN |
| 80 | 5-acetylenylpyridin-3-yl | $CO_2CH_3$ | CN |
| 81 | 5-acetylenylpyridin-3-yl | $CH_2CH_2CN$ | CN |
| 82 | 5-acetylenylpyridin-3-yl | $CH_2CN$ | CN |
| 83 | 5-acetylenylpyridin-3-yl | $CH_2C_6H_5$ | CN |
| 84 | 5-acetylenylpyridin-3-yl | $CH_2CH(CH_3)_2$ | CN |
| 85 | 5-acetylenylpyridin-3-yl | $CH_3$ | CN |
| 86 | 5-acetylenylpyridin-3-yl | $(CH_2)_2CF_3$ | CN |
| 87 | 6-chloropyrazin-2-yl | $CH_2CHF_2$ | CN |
| 88 | 6-chloropyrazin-2-yl | $CH_2CF_3$ | CN |
| 89 | 6-chloropyrazin-2-yl | H | CN |
| 90 | 6-chloropyrazin-2-yl | $CH_2CH=CH_2$ | CN |
| 91 | 6-chloropyrazin-2-yl | $CH_2C\equiv CH$ | CN |
| 92 | 6-chloropyrazin-2-yl | $CH_2C\equiv CCH_3$ | CN |
| 93 | 6-chloropyrazin-2-yl | $CH_2CO_2CH_3$ | CN |
| 94 | 6-chloropyrazin-2-yl | $CH(CH_3)CO_2CH_3$ | CN |
| 95 | 6-chloropyrazin-2-yl | $CO_2CH_3$ | CN |
| 96 | 6-chloropyrazin-2-yl | $CH_2CH_2CN$ | CN |
| 97 | 6-chloropyrazin-2-yl | $CH_2CN$ | CN |
| 98 | 6-chloropyrazin-2-yl | $CH_2C_6H_5$ | CN |
| 99 | 6-chloropyrazin-2-yl | $CH_2CH(CH_3)_2$ | CN |
| 100 | 6-chloropyrazin-2-yl | $(CH_2)_2CF_3$ | CN |
| 101 | 6-methoxypyrazin-2-yl | $CH_2CHF_2$ | CN |
| 102 | 6-methoxypyrazin-2-yl | $CH_2CF_3$ | CN |
| 103 | 6-methoxypyrazin-2-yl | H | CN |
| 104 | 6-methoxypyrazin-2-yl | $CH_2CH=CH_2$ | CN |
| 104 | 6-methoxypyrazin-2-yl | $CH_2C\equiv CH$ | CN |
| 106 | 6-methoxypyrazin-2-yl | $CH_2C\equiv CCH_3$ | CN |
| 107 | 6-methoxypyrazin-2-yl | $CH_2CO_2CH_3$ | CN |
| 108 | 6-methoxypyrazin-2-yl | $CH(CH_3)CO_2CH_3$ | CN |
| 109 | 6-methoxypyrazin-2-yl | $CO_2CH_3$ | CN |
| 110 | 6-methoxypyrazin-2-yl | $CH_2CH_2CN$ | CN |
| 111 | 6-methoxypyrazin-2-yl | $CH_2CN$ | CN |
| 112 | 6-methoxypyrazin-2-yl | $CH_2C_6H_5$ | CN |
| 113 | 6-methoxypyrazin-2-yl | $CH_2CH(CH_3)_2$ | CN |
| 114 | 6-methoxypyrazin-2-yl | $(CH_2)_2CF_3$ | CN |
| 115 | 5-chloropyridin-3-yl | $CH_2C_6H_5$ | H |
| 116 | 5-chloropyridin-3-yl | $CO(OCH_2CH_3)$ | CN |
| 117 | 5-chloropyridin-3-yl | $CO(OCH(CH_3))CO(OCH_3)$ | CN |

TABLE III

In Table III there are compounds of formula (I) wherein A is —CX'W—$CH_2$— and the groups Ar, R, X' and W are as given in Table III.

| Compound No. | Ar | R | $R^1$ | X' | W |
|---|---|---|---|---|---|
| 1 | 5-bromopyrid-3-yl | methyl | CN | exo-tert-butyl dimethylsilyloxy | H |
| 2 | 5-chloropyrid-3-yl | methyl | CN | exo-tert-butyl dimethylsilyloxy | H |
| 3 | 6-chloropyrazin-2-yl | methyl | CN | exo-tert-butyl dimethylsilyloxy | H |
| 4 | 5-bromopyrid-3-yl | methyl | CN | exo-hydroxy | H |
| 5 | 5-chloropyrid-3-yl | methyl | CN | exo-hydroxy | H |
| 6 | 6-chloropyrazin-2-yl | methyl | CN | exo-hydroxy | H |
| 7 | pyrid-3-yl | methyl | CN | exo-hydroxy | H |
| 8 | 5-bromopyrid-3-yl | methyl | CN | exo-F | H |
| 9 | 5-bromopyrid-3-yl | methyl | CN | =O | |
| 10 | 5-bromopyrid-3-yl | methyl | CN | F | F |
| 11 | 5-chloropyrid-3-yl | benzyl | CN | exo-tert-butyl dimethylsilyloxy | H |
| 12 | 5-chloropyrid-3-yl | benzyl | CN | exo-hydroxy | H |
| 13 | 5-chloropyrid-3-yl | benzyl | H | exo-CN | H |
| 14 | 5-chloropyrid-3-yl | benzyl | H | endo-CN | H |
| 15 | 5-chloropyrid-3-yl | benzyl | H | exo-tert-butyl dimethylsilyloxy | H |
| 16 | 5-chloropyrid-3-yl | benzyl | H | exo-hydroxy | H |
| 17 | 5-chloropyrid-3-yl | benzyl | H | =O | |

The preparation of the compounds of formula (I) may be accomplished by adaptation of methods described in the literature, by use of one or more of the following synthetic techniques described below and further illustrated in the Examples, or by combining literature methods with those methods described below. Throughout the following description $R^5$ is alkyl or phenylalkyl (especially benzyl).

Compounds of formula (I) can be prepared by treating compounds of formula (II) with a compound of formula RL where L is a suitable leaving group such as a halide or triflate, optionally in the presence of a suitable base, such as potassium carbonate.

Compounds of formula (I) wherein $R^1$ is other than cyano can be made by adapting methods described in the for either the conversion of a cyano group to the desired $R^1$ group or the replacement of a cyano group with the desired $R^1$ group.

Compounds of formula (II) (which are compounds of formula (I) wherein R is hydrogen) can be prepared by deprotecting compounds of formula (III) by, for instance, either: (i) treating them with a chloroformate ester (such as vinyl chloroformate) and subjecting the carbamate so formed to acid hydrolysis (with for example, hydrochloric acid); or (ii) treating them with an azodicarboxylate (such as diethyl azodicarboxylate) at a suitably elevated temperature.

A compound of formula (I) can be prepared by reacting a compound of formula (III) with a compound RHal (wherein Hal is a halogen) under suitable conditions (such as in the presence of a base and an alkali metal iodide) in a suitable solvent (such as N,N-dimethylformamide).

Alternatively, compounds of formula (I) can be prepared from compounds of formula (II) by reductive amination with an aldehyde ($R^6CHO$; where $R^6CH_2$=R) in the presence of a suitable reducing agent such as formic acid.

Compounds of formula (III) wherein $R^1$ is cyano can be prepared by treating compounds of formula (IV) first with a suitable base, such as lithium diisopropylamide (LDA) or lithium bis(trimethylsilyl)amide, and then reacting the product so formed with a compound ArHal, wherein Hal is a halogen.

Alternatively, compounds of formula (I) wherein $R^1$ is cyano can be prepared by treating compounds of formula (VI) with a suitable base, such as lithium diisopropylamide (LDA) or lithium bis(trimethylsilyl)amide, and reacting the product so formed with a compound ArHal, wherein Hal is a halogen.

Compounds of formula (VI) (wherein $R^1$ is cyano) can be prepared by treating compounds of formula (VII) with a suitable base, such as potassium carbonate, in the presence of a compound of formula RHal, wherein Hal is a halogen.

3-Cyano-9-methyl-9-azabicyclo[3.3.1]nonane (a compound of formula (IV) wherein A is $(CH_2)_3$ and $R^1$ is cyano) can be prepared by treating 3-oxo-9-methyl-9-azabicyclo [3.3.1]nonane with tosylmethyl isocyanide (also known as (4-tolylsulfonyl)methylisocyanide in the presence of a suitable base, such as potassium tert-butoxide.

3-Cyano-9-azabicyclo[3.3.1]nonane can be prepared by demethylating 3-cyano-9-methyl-9-azabicyclo[3.3.1] nonane by, for instance, treatment it with a chloroformate ester (such as vinyl chloroformate) and subjecting the carbamate so formed to acid hydrolysis.

As a further alternative, compounds of formula (VI), wherein $R^1$ is cyano, can be prepared by treating compounds of formula (VIII) with tosylmethyl isocyanide in the presence of a suitable base, such as potassium ethoxide.

Compounds of formula (VIII) can be prepared by a process analogous to the Robinson tropinone synthesis, from, for example, 2-ethoxy-3,4-dihydropyran. (See, for instance, Organic Synthesis (Collective Volume 4), p 816.)

Compounds of formula (I) wherein A is CH=CH can be prepared by heating a compound of fomula (I) wherein A is $CH_2CHZ$ (wherein Z is a suitable group, such as a thiono-4-tolyloxy group) in a suitable solvent (such as xylene) at a suitable temperature (such as reflux).

Compounds of formula (I) wherein A is $CH_2CHZ$ (wherein Z is a suitable group, such as a thiono-4-tolyloxy group) can be prepared by treating compounds of formula (I) wherein A is $CH_2CH(OH)$ with a suitable chloroformate (such as 4-tolyl chlorothionoformate) in the presence of a suitable base (such as N,N-dimethylaminopyridine).

Compounds of formula (I) wherein A is $CH_2CH(OH)$ can be prepared by acid hydrolysis of compounds of formula (I) wherein A is $CH_2CH(OZ')$ wherein Z' is a hydrolysable group (such as tert-butyldimethylsilyl).

A compound of formula (I) wherein A is $CH_2CH(OZ')$ wherein Z' is hydrogen or a hydrolysable group (such as tert-butyldimethylsilyl) and $R^1$ is cyano can be prepared by reacting a corresponding compound of formula (VI) with a suitable base, such as lithium diisopropylamide (LDA) or lithium bis(trimethylsilyl)amide, and reacting the product so formed with a compound ArHal, wherein Hal is a halogen.

A compound of formula (VI) wherein A is $CH_2CH(OZ')$ wherein Z' is hydrogen or a hydrolysable group (such as tert-butyldimethylsilyl) and $R^1$ is cyano can be prepared by treating a corresponding compound of formula (V) with tosylmethyl isocyanide (also known as (4-tolylsulfonyl) methylisocyanide in the presence of a suitable base, such as potassium tert-butoxide.

A compound of formula (V) wherein A is $CH_2CH(OZ')$ wherein Z' is a hydrolysable group (such as tert-butyldimethylsilyl) and $R^1$ is cyano can be prepared by reacting a compound of formula (V) wherein A is $CH_2CH$ (OH) and $R^1$ is cyano with a compound Z'L wherein L is a leaving group.

Alternatively a compound of formula (I) wherein A is CH=CH can be prepared by dehydrating a compound of formula (I) wherein A is $CH_2CH(OH)$ with a suitable dehydrating agent, such as diethylaminosulfurtrifluoride.

A compound of formula (I) wherein A is $CH_2CHF$ can be prepared by fluorinating a compound of formula (I) wherein A is $CH_2CH(OH)$ with, for example, a mixture of hydrogen fluoride and sulfur trifluoride.

A compound of formula (I) wherein A is $CH_2C(=O)$ can be prepared by reacting a compound of formula (I) wherein A is $CH_2CH(OH)$ with a suitable acid chloride (such as oxalyl chloride) at a suitable temperature (such as below −50° C.).

A compound of formula (I) wherein A is $CH_2CF_2$ can be prepared by fluorinating a compound of formula (I) wherein A is $CH_2C(=O)$ with, for example, diethylaminosulfurtrifluoride.

A compound of formula (I) wherein A is CH=CH can be prepared by reacting a compound of formula (I) wherein A is $CH_2CH(OZ')$, wherein Z' is a suitable group (such as $SO_2CH_3$) with a suitable amine (such as 1,8-diazabicyclo [5.4.0]undec-7-ene).

A compound of formula (I) wherein A is $CH_2CH(OZ')$, wherein Z' is a suitable group (such as $SO_2CH_3$) can be prepared by reacting a compound of formula (I) wherein A is $CH_2CH(OH)$ with a suitable acid chloride (such as mesyl chloride).

In further aspects the present invention provides processes for preparing compounds of formula (I), as hereinbefore described.

In a further aspect the invention provides a method of combating insect and like pests at a locus by applying to the locus or the pests an insecticidally effective amount of an insecticidal composition comprising a compound of formula (I) or an acid addition salt, quaternary ammonium salt or N-oxide derived therefrom.

The compounds of formula (I) can be used to combat and control infestations of insect pests such as Lepidoptera, Diptera, Homoptera and Coleoptera (including Diabrotica i.e. corn rootworms) and also other invertebrate pests, for example, acarine pests. The insect and acarine pests which may be combated and controlled by the use of the invention compounds include those pests associated with agriculture (which term includes the growing of crops for food and fibre products), horticulture and animal husbandry, forestry, the storage of products of vegetable origin, such as fruit, grain and timber, and also those pests associated with the transmission of diseases of man and animals. Examples of insect and acarine pest species which may be controlled by the compounds of formula (I) include: *Myzus persicae* (aphid), *Aphis gossypii* (aphid), *Aiphis fabae* (aphid), *Aedes aegypti* (mosquito), *Anopheles* spp. (mosquitos), *Culex* spp. (mosquitos), *Dysdercus fasciatus* (capsid), *Musca domestica* (housefly), *Pieris brassicae* (white butterfly), *Plutella xylostella* (diamond back moth), *Phaedon cochleariae* (mustard beetle), *Aonidiella* spp. (scale insects), *Trialeurodes* spp. (white flies), *Bemisia tabaci* (white fly), *Blattella germanica* (cockroach), *Periplaneta americana* (cockroach), *Blatta orientalis* (cockroach) *Spodoptera littoralis* (cotton leafworm), *Heliothis virescens* (tobacco budworm) *Chortiocetes terminifera* (locust), *Diabrotica* spp. (rootworms), *Agrotis* spp. (cutworms), *Chilo partellus* (maize stem borer), *Nilaparvata lugens* (planthopper), *Nephotettix cincticeps* (leafhopper), *Panonychus ulmi* (European red mite), *Panonychus citri* (citrus red mite), *Tetranychus urticae* (two-spotted spider mite), *Tetranychus cinnabarinus* (carmine spider mite), *Phyllcoptruta oleivora* (citrus rust mite), *Polyphagotarsonemus latus* (broad mite) and *Brevipalpus* spp. (mites). Further examples include insects which adversely affect the health of the public or of animals.

In order to apply the compounds of formula (I) to the locus of the nematode, insect or acarid pest, or to a plant susceptible to attack by the nematode, insect or acarid pest, the compound is usually formulated into a composition which includes in addition to a compound of formula (I) a suitable inert diluent or carrier material, and, optionally, a surface active agent. The amount of composition generally applied for the control of nematode pests gives a rate of active ingredient from 0.01 to 10 kg per hectare, preferably from 0.1 to 6 kg per hectare.

Thus in another aspect the present invention provides a insecticidal, acaricidal or nematicidal composition comprising an insecticidally, acaricidally or nematicidally effective amount of a compound of formula (I) and a suitable carrier or diluent therefor.

The compositions can be applied to the soil, plant or seed, to the locus of the pests, or to the habitat of the pests, in the form of dusting powders, wettable powders, granules (slow or fast release), emulsion or suspension concentrates, liquid solutions, emulsions, seed dressings, fogging/smoke formulations or controlled release compositions, such as microencapsulated granules or suspensions.

Dusting powders are formulated by mixing the active ingredient with one or more finely divided solid carriers and/or diluents, for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers.

Granules are formed either by absorbing the active ingredient in a porous granular material for example pumice, attapulgite clays, Fuller's earth, kieselguhr, diatomaceous earths, ground corn cobs, and the like, or on to hard core materials such as sands, silicates, mineral carbonates, sulphates, phosphates, or the like. Agents which are commonly used to aid in impregnation, binding or coating the solid carriers include aliphatic and aromatic petroleum solvents, alcohols, polyvinyl acetates, polyvinyl alcohols, ethers, ketones, esters, dextrins, sugars and vegetable oils. with the active ingredient. Other additives may also be included, such as emulsifying agents, wetting agents or dispersing agents.

Microencapsulated formulations (microcapsule suspensions CS) or other controlled release formulations may also be used, particularly for slow release over a period of time, and for seed treatment.

Alternatively the compositions may be in the form of liquid preparations to be used as dips, irrigation additives or sprays, which are generally aqueous dispersions or emulsions of the active ingredient in the presence of one or more known wetting agents, dispersing agents or emulsifying agents (surface active agents). The compositions which are to be used in the form of aqueous dispersions or emulsions are generally supplied in the form of an emulsifiable concentrate (EC) or a suspension concentrate (SC) containing a high proportion of the active ingredient or ingredients. An EC is a homogeneous liquid composition, usually containing the active ingredient dissolved in a substantially non-volatile organic solvent. An SC is a fine particle size dispersion of solid active ingredient in water. In use, the concentrates are diluted in water and applied by means of a spray to the area to be treated.

Suitable liquid solvents for ECs include methyl ketones, methyl isobutyl ketone, cyclohexanone, xylenes, toluene, chlorobenzene, paraffins, kerosene, white oil, alcohols, (for example, butanol), methylnaphthalene, trimethylbenzene, trichloroethylene, N-methyl-2-pyrrolidone and tetrahydrofurfuryl alcohol (THFA).

Wetting agents, dispersing agents and emulsifying agents may be of the cationic, anionic or non-ionic type. Suitable agents of the cationic type include, for example, quaternary ammonium compounds, for example cetyltrimethyl ammonium bromide. Suitable agents of the anionic type include, for example, soaps, salts of aliphatic monoesters of sulphuric acid, for example sodium lauryl sulphate, salts of sulphonated aromatic compounds, for example sodium dodecylbenzenesulphonate, sodium, calcium or ammonium lignosulphonate, or butylnaphthalene sulphonate, and a mixture of the sodium salts of diisopropyl- and triisopropyl-naphthalene sulphonates. Suitable agents of the non-ionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids and hexitol anhydrides, the condensation products of the said partial esters with ethylene oxide, and the lecithins.

These concentrates are often required to withstand storage for prolonged periods and after such storage, to be capable of dilution with water to form aqueous preparations which remain homogeneous for a sufficient time to enable them to be applied by conventional spray equipment. The concentrates may contain 10–85% by weight of the active ingredient or ingredients. When diluted to form aqueous preparations such preparations may contain varying amounts of the active ingredient depending upon the purpose for which they are to be used.

The compounds of formula (I) may also be formulated as powders (dry seed treatment DS or water dispersible powder WS) or liquids (flowable concentrate FS, liquid seed treatment LS, or microcapsule suspension CS) for use in seed treatments.

In use the compositions are applied to the insect pests, to the locus of the pests, to the habitat of the pests, or to growing plants liable to infestation by the pests, by any of the known means of applying pesticidal compositions, for example, by dusting, spraying, or incorporation of granules.

The compound of formula (I) may be the sole active ingredient of the composition or it may be admixed with one or more additional active ingredients such as insecticides, synergists, herbicides, fungicides or plant growth regulators where appropriate. Suitable additional active ingredients for inclusion in admixture with a compound of formula (I) may be compounds which will broaden the spectrum of activity of the compositions of the invention or increase their persistence in the location of the pest. They may synergise the activity of the compound of formula (I) or complement the activity for example by increasing the speed of effect or overcoming repellency. Additionally multi-component mixtures of this type may help to overcome or prevent the development of resistance to individual components. The particular additional active ingredient included will depend upon the intended utility of the mixture and the type of complementary action required. Examples of suitable insecticides include the following:

a) Pyrethroids such as permethrin, esfenvalerate, deltamethrin, cyhalothrin in particular lambda-cyhalothrin, biphenthrin, fenpropathrin, cyfluthrin, tefluthrin, fish safe pyrethroids for example ethofenprox, natural pyrethrin, tetramethrin, s-bioallethrin, fenfluthrin, prallethrin and 5-benzyl-3-furylmethyl-(E)-(1R,3S)-2,2-dimethyl-3-(2-oxothiolan-3-ylidenemethyl) cyclopropane carboxylate;

b) Organophosphates such as profenofos, sulprofos, methyl parathion, azinphos-methyl, demeton-s-methyl, heptenophos, thiometon, fenamiphos, monocrotophos, profenophos, triazophos, methamidophos, dimethoate, phosphamidon, malathion, chloropyrifos, phosalone, terbufos, fensulfothion, fonofos, phorate, phoxim, pyrimiphos-methyl, pyrimiphos-ethyl, fenitrothion or diazinon;

c) Carbamates (including aryl carbamates) such as pirimicarb, cloethocarb, carbofuran, furathiocarb, ethiofencarb, aldicarb, thiofurox, carbosulfan, bendiocarb, fenobucarb, propoxur or oxamyl;

d) Benzoyl ureas such as triflumuron, or chlorfluazuron;

e) Organic tin compounds such as cyhexatin, fenbutatin oxide, azocyclotin;

f) Macrolides such as avermectins or milbemycins, for example such as abamectin, ivermectin, and milbemycin;

g) Hormones and pheromones;

h) Organochlorine compounds such as benzene hexachloride, DDT, chlordane or dieldrin;

i) Amidines, such as chlordimeform or amitraz;

j) Fumigant agents;

k) Imidacloprid;

l) Spinosad.

In addition to the major chemical classes of insecticide listed above, other insecticides having particular targets may be employed in the mixture if appropriate for the intended utility of the mixture. For instance selective insecticides for particular crops, for example stemborer specific insecticides for use in rice such as cartap or buprofezin can be employed. Alternatively insecticides specific for particular insect species/stages for example ovo-larvicides such as chlofentezine, flubenzimine, hexythiazox and tetradifon, motilicides such as dicofol or propargite, acaricides such as bromopropylate, chlorobenzilate, or growth regulators such as hydramethylron, cyromazine, methoprene, chlorofluazuron and diflubenzuron may also be included in the compositions.

Examples of suitable synergists for use in the compositions include piperonyl butoxide, sesamax, safroxan and dodecyl imidazole.

Suitable herbicides, fungicides and plant-growth regulators for inclusion in the compositions will depend upon the intended target and the effect required.

An example of a rice selective herbicide which can be included is propanil, an example of a plant growth regulator for use in cotton is "Pix", and examples of fungicides for use in rice include blasticides such as blasticidin-S. The ratio of the compound of formula (I) to the other active ingredient in the composition will depend upon a number of factors including type of target, effect required from the mixture etc. However in general, the additional active ingredient of the composition will be applied at about the rate at which it is usually employed, or at a slightly lower rate if synergism occurs.

The invention is illustrated by the following Examples. Examples 1≧27 illustrate the preparation of a range of compounds of formula (I). Examples 28–35 illustrate compositions suitable for the application of the compounds of formula (I) according to the invention. The following ingredients are referred to by their Registered Trade Marks and have the composition as shown below.

| Registered Trade Mark | Composition |
| --- | --- |
| Synperonic NP8 } | Nonylphenol-ethylene oxide condensate |
| Synperonic NP13 } | |
| Synperonic OP10 } | |
| Aromasol H | Alkylbenzene solvent |
| Solvesso 200 | Inert organic diluent |
| Keltrol | Polysaccharide |

Selected NMR data and melting point data are presented in the Examples. For NMR data, no attempt has been made to list every absorption. The following abbreviations are used throughout the Examples:

| | |
| --- | --- |
| mp = melting point (uncorrected) | ppm = parts per million |
| s = singlet | t = triplet |
| d = doublet | q = quartet |
| dd = double doublet | dt = double triplet |
| tt = triple triplet | brd = broad doublet |
| m = multiplet | |

EXAMPLE 1

This Example illustrates the preparation of exo-3-(5-chloropyrid-3-yl)-endo-3-cyano-9-methyl-9-azabicyclo[3.3.1]nonane (Compound No. 26 Table I).

Stage 1

9-Methyl-9-azabicyclo[3.3.1]non-3-one$^{1,2}$ (5.6 g), (4-tolylsulfonyl)methylisocyanide (8.8 g) and anhydrous ethanol (10 ml) in dry dimethoxyethane (150 ml) were cooled to 0° C. under nitrogen. Potassium tert-butoxide (10.1 g) was added to the stirred solution at such a rate so as to maintain the temperature below 10° C. On complete addition the mixture was allowed to reach ambient temperature and was stirred for 40 hours. Further (4-tolylsulfonyl)methylisocyanide (19 g) and potassium tert-butoxide (1.2 g) were added in portions over the next 5 days to complete the reaction. The solvent was evaporated under reduced pressure, the residue treated with aqueous sodium carbonate and extracted with ethyl acetate (2×250 ml). The combined organic extracts were washed with aqueous sodium carbonate, dried (magnesium sulfate) and the solvent evaporated under reduced pressure to give a brown oil. The oil was extracted repeatedly with hot hexane and the combined extracts evaporated under reduced pressure and the residue was fractionated by chromatography (silica, 2% methanol in dichloromethane) to give exo-3-cyano-9-methyl-9-azabicyclo[3.3.1]nonane (1.1 g).

$^1$H NMR (CDCl$_3$): δ 1.45–1.58(2H,m); 1.60–1.65(2H,m); 1.80–1.90(2H,m); 2.00–2.15(2H,m); 2.20–2.35(2H,m); 2.50 (3H,s); 2.88(2H,m); 3.25–3.40(1H,m)ppm.

References

1. A. T. Bottini and J. Gal J. Org. Chem. 36 1718 (1971)
2. J. R. Wiseman, H. O. Krabbenhoft, R. E. Lee J. Org. Chem. 42 629 (1977)

Stage 2 exo-3 -Cyano-9-methyl-9-azabicyclo[3.3.1]nonane (0.9 g) and 3,5-dichloropyridine (0.89 g) in dry tetrahydrofuran (10 ml) were stirred at ambient temperature under nitrogen and treated dropwise with lithium bis(trimethylsilyl)amide (7 ml of a solution in tetrahydrofuran, 1M). The reaction was kept at ambient temperature for 18 hours and the solvent evaporated under reduced pressure. The residue was dissolved in ethyl acetate (50 ml), extracted with hydrochloric acid (2×50 ml, 2M), the combined aqueous fractions separated, basified with potassium carbonate followed by extraction with ethyl acetate (2×50 ml). The organic fractions were dried (magnesium sulfate), evaporated under reduced pressure to give a brown oil which was fractioned using thick layer chromatography (silica, 10% methanol in dichloromethane) to give the required product (0.36 g) as a waxy solid, mp 110–114° C.

$^1$H NMR (CDCl$_3$): δ 1.15–1.25(2H,m); 1.90–2.30(9H,m); 2.90(2H,m); 3.00(2H,m); 7.75(1H,m); 8.45(1H,d); 8.60(1H, d)ppm.

EXAMPLE 2

This Example illustrates the preparation of 9-(3-chlorobenzyl)-exo-3-cyano-9-azabicyclo[3.3.1]nonane.

Stage 1

2-Ethoxy-3,4-dihydropyran (38.4 g) in water (120 ml) was stirred at ambient temperature and treated with concentrated hydrochloric acid (13.2 ml) for 1 hour to give a colourless solution of glutaraldehyde. 3-Chlorobenzylamine (42.5 g) was treated with concentrated hydrochloric acid (30 ml) and water (200 ml) to give a suspension of the hydrochloride salt which was added to the above at ambient temperature. Acetone 1,3-dicarboxylic acid (49.8 g) in water (400 ml) was added to the mixture followed by a buffer solution prepared from disodium hydrogen phosphate (23.3 g) and sodium hydroxide (4.5 g) in water (120 ml). Tetrahydrofuran (200 ml) was added to dissolve the gum which was produced and the mixture stirred for 18 hours, after which time gas evolution had ceased. The reaction mixture was treated with saturated aqueous sodium carbonate to give a solution of pH10, which was extracted with diethyl ether (2×500 ml). The extracts were combined, washed with water, dried (magnesium sulfate) and evaporated under reduced pressure to give a gum which was fractionation by eluting through a column of silica using hexane/ethyl acetate [from 5% to 30% ethyl acetate by volume] to give 9-(3-chlorobenzyl)-9-azabicyclo[3.3.1]non-3-one, 35 g, mp 74–5° C.

$^1$H NMR (CDCl$_3$): δ 1.55(4H,m); 1.95(2H,m); 2.28(2H, d); 2.75(2H,dd); 3.30(2H,m); 3.90(2H,s); 7.25(3H,m); 7.43 (1H,m)ppm.

Stage 2

Potassium tert-butoxide (6.4 g) was dissolved with stirring in dry 1,2-dimethoxyethane (60 ml) and cooled to 0° C. under an atmosphere of nitrogen. 4-Tolylsulfonyl methyl isocyanide (8.0 g) in dry 1,2-dimethoxyethane (80 ml) was added slowly at 0° C. and stirred for 1 hour. The material from Stage 1 (5.0 g) in dry 1,2-dimethoxyethane (40 ml) was added slowly over 2 hours, the reaction was allowed to gradually warm to ambient temperature and was stirred for an additional 18 hours. Further 4-tolylsulfonyl methylisocyanide (2.0 g) was added to the reaction mixture which was stirred for another 4 hours. Water (100 ml) was added, the solvent evaporated under reduced pressure to give a brown oil which was partitioned between water (200 ml) and ethyl acetate (200 ml), the phases separated and the aqueous fraction re-extracted with ethyl acetate (3×200 ml). The combined organic phase was washed with saturated aqueous sodium chloride solution (100 ml), dried (magnesium sulfate) and evaporated under reduced pressure to give a dark brown oil which was fractionated by eluting through a column of silica with 20% ethyl acetate/hexane to give the required product as a colourless oil, 1.7 g.

$^1$H NMR (CDCl$_3$): δ 1.50(2H,m); 1.70(2H,m); 1.90(2H, m); 2.00(2H,m); 2.20(2H,m); 2.85(2H,broad m); 3.35(1H, m); 3.80(2H,s); 7.20(3H,m); 7.40(1H,s)ppm.

The following ketones were prepared using a procedure similar to Example 2, Stage 1:

9-(2-Methylpropyl)-9-azabicyclo[3.3.1]non-3-one: $^1$H NMR (CDCl$_3$): δ 0.90(6H,d); 1.50(4H,m);1.70(1H,m); 1.90 (2H,m); 2.20(2H,d); 2.40(2H,d); 2.65(2H,dd); 3.30(2H,m) ppm.

9-Allyl-9-azabicyclo[3.3.1]non-3-one: $^1$H NMR (CDCl$_3$): δ 1.50(4H,m); 1.90(2H,m); 2.20(2H,d); 2.70(2H, dd); 3.35(4H,dd); 5.15(1H,dd); 5.25(1H,dt); 5.90(1H,m) ppm.

9-(2,2,2-Trifluoroethyl)-9-azabicyclo[3.3.1]non-3-one: $^1$H NMR (CDCl$_3$): δ 1.60(4H,m); 1.90(2H,m); 2.30(2H,dd); 2.70(2H,dd); 3.20(2H,q); 3.40(2H,m)ppm.

The following nitriles were prepared from the corresponding ketones using a procedure similar to Example 2, Stage 2:

exo-9-Benzyl-3-cyano-9-azabicyclo[3.3.1]nonane: $^1$H NMR (CDCl$_3$): δ 1.42–1.55(2H,m); 1.68–1.80(2H,m); 1.85–1.94(2H,m); 2.00–2.15(2H,m); 2.18–2.30(2H,m); 2.85–2.92(2H,m); 3.30–3.45(1H,m); 3.85(2H,s); 7.20–7.40 (5H,m)ppm, obtained from 9-benzyl-9-azabicyclo[3.3.1] non-3-one[2].

9-Allyl-exo-3-cyano-9-azabicyclo[3.3.1]nonane: $^1$H NMR (CDCl$_3$): δ 1.50(2H,m); 1.70(2H,m); 1.85(2H,m); 2.00(2H,m); 2.20(2H,m); 2.90(2H,m); 3.30(2Hdd); 3.35 (1H,m); 5.10(1H,dd); 5.20(1H,dt); 5.80(1H,m)ppm.

exo-3-Cyano-9-(2-methylpropyl)-9-azabicyclo[3.3.1] nonane: $^1$H NMR (CDCl$_3$): δ 0.9(6H,d); 1.45(2H,m); 1.60 (1H,m); 1.70(2H,m); 1.85(2H,m); 2.00(2H,m); 2.20(2Hm); 2.35(2H,d); 2.80(2H,m); 3.30(1H,m)ppm.

exo-3-Cyano-9-(2,2,2-trifluoroethyl)-9-azabicyclo[3.3.1] nonane: $^1$H NMR (CDCl$_3$) δ 1.50(2H,m); 1.70(2H,m); 1.90 (4H,dd); 2.20(2H,m); 2.90(2H,broad q); 3.10(2H,q); 3.35 (1H,m)ppm.

Using a procedure similar to Example 1, Stage 2 the following were prepared from the corresponding nitriles:

9-Benzyl-exo-3-(5-chloropyrid-3-yl)-endo-3-cyano-9-azabicyclo[3.3.1]nonane (Compound No. 27 Table I), (colourless oil): $^1$H NMR (CDCl$_3$): δ 1.15(2H,m); 1.95–2.30 (6H,m); 2.85–3.10(4H,m); 3.60(2H,s); 6.60(2H,m); 7.15 (3H,m); 7.68(1H,m); 8.55(1H,d); 8.64(1H,d)ppm.

9-Allyl-exo-3-(5-chloropyrid-3-yl)-endo-3-cyano-9-azabicyclo[3.3.1]nonane (Compound No. 6 Table I).

9-(3-Chlorobenzyl)-exo-3-(5-chloropyrid-3-yl)-endo-3-cyano-9-azabicyclo[3.3.1]nonane (Compound No. 7 Table I).

exo-3-(5-Chloropyrid-3-yl)-endo-3-cyano-9-(2,2,2-trifluoroethyl)-9-azabicyclo[3.3.1]nonane, (Compound No. 28 Table I): $^1$H NMR (CDCl$_3$): δ 1.30(2H,dd);1.60–1.90 (6H,m); 2.30(2H,dd); 3.00(2H,q); 3.15(2H,broad m); 7.50 (1H,t); 8.50(1H,d); 8.65(1H,d)ppm.

exo-3-(5-Chloropyrid-3-yl)-endo-3-cyano-9-(2-methylpropyl)-9-azabicyclo[3.3.1]nonane (Compound No. 5 Table I).

exo-3-(6-Chloropyrazin-2-yl)-endo-3-cyano-9-(2,2,2-trifluoroethyl)-9-azabicyclo[3.3.1]nonane, (Compound No. 29 Table I): $^1$H NMR (CDCl$_3$): δ 1.25(2H,m); 1.70(3H,m); 2.10(1H,m); 2.20(2H,m); 3.10(2H,broad multiplet); 3.45 (2H,m), 3.85(2H,q); 8.45(1H,s); 8.75(1H,s)ppm.

EXAMPLE 3

This Example illustrates the preparation of exo-3-(5-chloropyrid-3-yl)-endo-3-cyano-9-carbonyloxyvinyl-9-azabicyclo[3.3.1]nonane (Compound No. 30 Table I).

exo-3-(5-Chloropyrid-3-yl)-endo-3-cyano-9-methyl-9-azabicyclo[3.3.1]nonane (1.0 g) was dissolved in dry 1,2- dichloroethane (15 ml) at 0° C. with stirring under an atmosphere of nitrogen and treated with a solution of vinyl chloroformate (0.45 g) in dry 1,2-dichloroethane (5 ml). The reaction mixture was allowed to warm to ambient temperature, stirred for 1 hour, 4-N,N-dimethylaminopyridine (0.005 g) added, stirred for a further 2 hours and heated to reflux for 18 hours. The mixture was cooled to ambient temperature, partioned between diethyl ether (200 ml) and hydrochloric acid (2M), the organic phase separated and washed with water, dried (magnesium sulfate) and evaporated under reduced pressure to give the required product as a pale brown gum, 0.36 g.

$^1$H NMR (CDCl$_3$): δ 1.30(2H,m); 1.70(2H,m); 2.15(2H, m); 2.30(2H,m); 2.95(2H,m); 4.55(2H,m); 4.42(1H,dd); 4.68(1H,dd); 6.85(1H,dd); 7.70(1H,dd); 8.50(1H,d); 8.60 (1H,d)ppm.

EXAMPLE 4

This Example illustrates the preparation of exo-3-(5-chloropyrid-3-yl)-endo-3-cyano-9-azabicyclo[3.3.1]nonane (Compound No. 31 Table I).

The product from Example 3 (0.24 g) was dissolved in methanol (1 ml) containing hydrochloric acid (5 ml, 2M) with stirring and heated to 90–100° C. for 2.5 hours. The reaction was cooled to ambient temperature, basified with a saturated, aqueous solution of sodium carbonate, and extracted with ethyl acetate (2×100 ml). The combined organic phase was dried (magnesium sulfate) and evaporated under reduced pressure to give a gum which was fractionated by preparative thick layer chromatography (silica, 10% methanol in dichloromethane) to give the required product as a pale brown gum, 0.052 g. Molecular ion 261.

EXAMPLE 5

This Example illustrates the preparation of exo-7-(5-chloropyrid-3-yl)-endo-7-cyano-9-aza-9-methyl-3-oxabicyclo[3.3.1]nonane (Compound No. 4 Table I).

Stage 1

Hydroxyacetaldehyde diethylacetal (3.75 g) was added to sodium hydride (0.8 g, 80% in mineral oil) in tetrahydrofuran (100 ml) under an atmosphere of nitrogen. The mixture was stirred and bromoacetaldehyde diethyl acetal (5.0 g) and potassium iodide (0.1 g) were added. The mixture was heated to reflux for 16 hours, water added and evaporated under reduced pressure. The residue was dissolved in diethyl ether, the organic phase washed with water, dried (MgSO$_4$) and evaporated under reduced pressure to give bis(2,2-diethoxyethyl)ether, 3.43 g, as a yellow oil.

$^1$H NMR (CDCl$_3$): δ 1.20(12H,t); 3.60(8H,d); 3.70(4H, q); 4.60(2H,t)ppm.

Stage 2

Bis(2,2-diethoxyethyl)ether (3.4 g) was heated to reflux with glacial acetic acid (0.9 ml) and water (3.5 ml) for 45 minutes with stirring. The mixture was cooled, added to a solution of disodium orthophosphate (13.3 g) and citric acid (3.45 g) in water (80 ml) and acetone dicarboxylic acid (4.9 g) and methylamine hydrochloride (2.03 g) added. The mixture was adjusted to pH 5 by addition of 50% sodium hydroxide solution and stirred for 48 hours at ambient temperature. The orange brown solution was acidified by addition of concentrated hydrochloric acid and washed with diethyl ether. The aqueous layer was separated, basified with aqueous sodium hyroxide and extracted with dichloromethane 10×80 ml). The combined organic phase was dried (MgSO$_4$) and evaporated under reduced pressure to give 9-aza-9-methyl-3-oxabicyclo[3.3.1]non-7-one, 1.15 g, as an orange solid, mp 64–67° C.

Stage 3

Potassium tert-butoxide (5.44 g) was stirred in dry 1,2-dimethoxyethane (30 ml) at 0° C. under an atmosphere of nitrogen and (4-tolylsulfony)methylisocyanide (6.37 g) in dry 1,2-dimethoxyethane (80 ml) was added dropwise, keeping the temperature below 5° C. The reaction mixture was stirred for 1 hour at 0° C., 9-aza-9-methyl-3-oxabicyclo[3.3.1]non-7-one (2.50 g) in dry 1,2-dimethoxyethane (40 ml) added slowly over 1.5 hour, the mixture allowed to warm to ambient temperature and stirred for 18 hours. The reaction mixture was evaporated under reduced pressure, the residue was partitioned between a saturated, aqueous solution of sodium chloride and ethyl acetate. The organic phase was separated, dried (magnesium sulfate) and evaporated under reduced pressure to give a brown oil which was fractionated by chromatography (silica, 2% methanol in dichloromethane) to give 9-aza-exo-7-cyano-9-methyl-3-oxabicyclo[3.3.1]nonane, 1.12 g, as a brown oil.

$^1$H NMR (CDCl$_3$): δ 3.96(2H,dt); 3.90(1H,tt); 3.75(2H, dd); 2.65(2H,m); 2.55(3H,s); 2.29(2H,m,); 1.90(2H,m)ppm.

Stage 4 exo-7-Cyano-9-aza-3-oxabicyclo[3.3.1]nonane (0.20 g) and 3,5-dichloropyridine (0.21 g) were dissolved with stirring in dry tetrahydrofuran (5 ml) under an atmosphere of nitrogen at ambient temperature. Lithium bis(trimethylsilyl) amide (1.3 ml of a tetrahydrofuran solution, 1M) was added dropwise over 2 hours and the reaction mixture was stirred for 18 hours. The reaction mixture was quenched with water (2 ml), evaporated under reduced pressure and the brown residue partitioned between a saturated, aqueous solution of sodium chloride and ethyl acetate. The organic phase was separated, dried (MgSO$_4$) and evaporated under reduced pressure to give a yellow oil which was fractionated by chromatography (silica, 10% ethanol in ethyl acetate) to give the required product as a pale yellow solid, 0.055 g.

$^1$H NMR (CDCl$_3$): δ 8.80(1H,d); 8.60(1H,d); 8.00(1H, dd); 4.10(2H,dt); 3.90(2H,d); 2.80(2H,m); 2.55(3H,s); 2.50 (2H,dd); 2.30(2H,d)ppm.

exo-7-(5-Bromopyrid-3-yl)-endo-7-cyano-9-aza-9-methyl-3-oxabicyclo[3.3.1]nonane was prepared in a similar procedure using 3,5-dibromopyridine (Compound No. 9 Table I): $^1$H NMR (CDCl$_3$): δ 8.85(1H,broad d); 8.65(1H, broad d); 8.10(1H,t); 4.10(2H,dt); 3.90(2H,d); 2.80(2H,m); 2.55(3H,s); 2.50(2H,dd); 2.30(2H,d)ppm.

EXAMPLE 6

This Example illustrates the preparation of exo-3-(5-bromopyrid-3-yl)-endo-3-cyano-8-methyl-8-azabicyclo [3.2.1]oct-6-ene (Compound No. 1 Table II).

Stage 1

Imidazole (4.39 g) was added to a stirred solution of tert-butyldimethylsilyl chloride (4.87 g) in dry N,N-dimethylformamide (25 ml) at ambient temperature. exo-6-Hydroxy-8-methyl-8-azabicyclo[3.2.1]octan-3-one (Ref. 3; 5.0 g) in dry N,N-dimethylformamide (25 ml) was added, the mixture stirred for 1 hour and stored for 18 hours. The reaction was poured into water, extracted with diethyl ether (three times), the combined organic phase washed with saturated aqueous sodium chloride, dried (magnesium sulfate) and evaporated under reduced pressure to give exo-6-tert-butyldimethylsilyloxy-8-methyl-8-azabicyclo [3.2.1]octan-3-one, as a pale yellow oil, 8.7 g.

¹H NMR (CDCl₃): δ 0.05(6H,s); 0.90(9H,s); 2.00–2.30 (4H,m); 2.60–2.70(2H,m); 2.68(3H,s); 3.35(1H,m); 3.60 (1H,m); 4.10(1H,m)ppm.

Ref 3: P. Nedenskov, N. Clauson-Kaas, Acta. Chem. Scand. 8, 1295, (1954).

Stage 2

Potassium tert-butoxide (10.84 g) was stirred in dry 1,2-dimethoxyethane (25 ml) at 0° C. under an atmosphere of nitrogen and a solution of 4-tolylsulfonylmethylisocyanide (12.58 g) in dry 1,2-dimethoxyethane (25 ml) was added dropwise, maintaining the reaction temperature below 10° C. On complete addition the mixture was stirred at 0° C. for 45 minutes and a solution of exo-6-tert-butyldimethylsilyloxy-8-methyl-8-azabicyclo [3.2.1]octan-3-one (8.58 g) in dry 1,2-dimethoxyethane (40 ml) was added dropwise. The reaction was stirred at 0° C. for a further 1 hour, allowed to warm to ambient temperature and was stirred for 18 hours. The reaction was neutralised with hydrochloric acid (2M) and the mixture evaporated under reduced pressure to give a brown solid. The solid was extracted with hexane (three times) and the combined hexane extracts evaporated under reduced pressure to give exo-6-tert-butyldimethylsilyloxy-exo-3-cyano-8-methyl-8-azabicyclo[3.2.1]octane, (7.10 g), as a yellow oil.

¹H NMR (CDCl₃): δ 0.05(6H,s); 0.80(9H,s); 1.55–2.15 (6H,m); 2.35–2.50(1H,m); 2.49(3H,s); 2.95(1H,m); 3.30 (1H,m); 4.10(1H,m)ppm.

Stage 3

The product from Stage 2 (6.70 g) was dissolved in dry tetrahydrofuran (70 ml) containing 3,5-dibromopyridine (5.75 g) at 0° C. under an atmosphere of nitrogen with stirring. Lithium bis-(trimethylsilyl) amide (24.3 ml of a tetrahydrofuran solution, 1M) was added dropwise to the solution, maintaining the reaction temperature below 5° C. The reaction was stirred at 0° C. for 1 hour and allowed to warm to ambient temperature for 2 days. The reaction mixture was treated with further 3,5-dibromopyridine (0.86 g), stirred for 7 hours and stored for 18 hours. The mixture was poured into water, extracted with ethyl acetate (three times), the combined organic phase dried (magnesium sulfate) and evaporated under reduced pressure to give a brown oil. The oil was fractionated by chromatography (silica, 5–10% methanol by volume in dichloromethane) to give exo-3-(5-bromopyrid-3-yl)-exo-6-tert-butyldimethylsilyloxy-endo-3-cyano-8-methyl-8-azabicyclo[3.2.1]octane (Compound No. 1 Table III), 6.19 g, as a colourless solid, mp 86–7° C.

¹HNMR (CDCl₃): δ 0.15(6H,s); 0.90(9H,s); 2.10–2.35 (5H,m); 2.60(3H,s); 2.80(1H,q); 3.20(1H,m); 3.55(1H,m); 5.00(1H,m); 7.99(1H,t); 8.60(1H,d); 8.72(1H,d)ppm.

exo-6-tert-Butyldimethylsilyloxy-exo-3-(5-chloropyrid-3-yl)-3-endo-cyano-8-methyl-8-azabicyclo[3.2.1]octane (Compound No. 2 Table III), colourless solid; mp 82.5–83.5° C.; ¹H NMR (CDCl₃) δ 0.12(6H,s); 0.90(9H,s); 2.10–2.40(5H,m); 2.60(3H,s); 2.80(1H,q); 3.20(1H,m); 3.55 (1H,m); 5.00(1H,m); 7.85(1H,t); 8.52(1H,d); 8.70(1H,d) ppm was prepared in a similar procedure from 3,5-dichloropyridine.

exo-6-tert-Butyldimethylsilyloxy-exo-3-(6-chloropyrazin-2-yl)-endo-3-cyano-8-methyl-8-azabicyclo [3.2.1]octane (Compound No. 3 Table III); pale yellow solid; ¹H NMR (CDCl₃): δ 0.15(6H,s); 0.90(9H,s); 2.00–2.30(3H,m); 2.50(2H,d); 2.60(3H,s); 2.80(1H,dd); 3.22(1H,m); 3.55(1H,m); 5.00 (1H,m); 8.58(1H,s); 8.80(1H, s)ppm was prepared in a similar procedure from 2,6-dichloropyrazine.

Stage 4 exo-3-(5-Bromopyrid-3-yl)-exo-6-tert-butyldimethylsilyloxy-endo-3-cyano-8-methyl-8-azabicyclo[3.2.1]octane (1.0 g) in tetrahydrofuran (2 ml) was treated with aqueous hydrochloric acid (5 ml, 4M) with stirring at ambient temperature for 20 hours. The mixture was neutralised with aqueous sodium carbonate solution and evaporated under reduced pressure. The residual solid was extracted with propan-2-ol, insolubles were filtered from solution and the filtrate was evaporated under reduced pressure. The residue was washed with hexane and filtered to give exo-3-(5-bromopyrid-3-yl)-endo-3-cyano-exo-6-hydroxy-8-methyl-8-azabicyclo[3.2.1]octane (Compound No. 4 Table III), 0.45 g, as a colourless solid, mp 191.5–193.5° C.

¹H NMR(CDCl₃): δ 2.00–2.35(5H,m); 2.60(3H,s); 2.90 (1H,q); 3.30(1H,s); 3.55(1H,m); 5.00(1H,m); 8.00(1H,t); 8.65(1H,d); 8.75(1H,d)ppm.

exo-3-(5-Chloropyrid-3-yl)-endo-3-cyano-exo-6-hydroxy-8-methyl-8-azabicyclo[3.2.1]octane (Compound No. 5 Table III), colourless solid, mp 172–5° C., was prepared in a similar procedure. ¹H NMR (CDCl₃): δ 2.00–2.40(5H,m); 2.60(3H,s); 2.90(1H,q); 3.30(1H, broad s); 3.55(1H,m); 5.00(1H,m); 7.85(1H,t); 8.55(1H,d); 8.70 (1H,d)ppm. Molecular ion (MH⁺) 278.

exo-3-(6-Chloropyrazin-2-yl)-endo-3-cyano-exo-6-hydroxy-8-methyl-8-azabicyclo[3.2.1]octane (Compound No. 6 Table III), colourless solid, mp 179–180° C., was prepared using a similar procedure. ¹H NMR (CDCl₃): δ 1.85(1H,dd); 2.00(1H,dd); 2.05–2.20(1H,m); 2.20–2.30(1H, m); 2.50–2.70(2H,m); 2.60(3H,s); 2.95(1H,q); 3.30(1H,m); 3.55(1H,m); 4.90(1H,m); 8.60(1H,s); 8.85(1H,s)ppm. Molecular ion 278.

Stage 5 exo-3-(5-Bromopyrid-3-yl)-endo-3-cyano-exo-6-hydroxy-8-methyl-8-azabicyclo-[3.2.1]octane (0.500 g) was stirred in dry dichloromethane (5 ml) and treated with 4-N,N-dimethylaminopyridine (0.209 g) and 4-tolyl chlorothionoformate (0.29 ml) at ambient temperature. The reaction was stirred for 10 hours and stored for 2 days. The mixture was diluted with hexane, filtered and the filtrate evaporated under reduced pressure. The residue was fractionated by chromatography (silica; dichloromethane—5% methanol by volume in dichloromethane) to give exo-3-(5-bromopyrid-3-yl)-endo-3-cyano-8-methyl-exo-6-(thiono-4-tolyloxy)-8-azabicyclo[3.2.1]octane, 0.44 g, as a colourless glassy solid.

¹HNMR(CDCl₃): δ 2.20–2.40(3H,m); 2.39(3H,s); 2.50–2.65(2H,m); 2.55(3H,s); 3.00(1H,q); 3.60–3.70(2H, m); 6.25(1H,m); 7.00(2H,d); 7.20(2H,d); 8.00(1H,t); 8.65 (1H,d); 8.75(1H,d)ppm.

exo-3-(5-Chloropyrid-3-yl)-endo-3-cyano-8-methyl-exo-6-(thiono-4-tolyloxy)-8-azabicyclo[3.2.1]octane, colourless solid, was prepared from the corresponding intermediate in a similar manner.

exo-3-(6-Chloropyrazin-2-yl)-endo-3-cyano-8-methyl-exo-6-(thiono-4-tolyloxy)-8-azabicyclo[3.2.1]octane, colourless solid, was prepared from the corresponding intermediate in a similar manner.

Stage 6

The product from Stage 5 (0.43 g) was dissolved in dry xylene (10 ml) and heated to reflux for 18 hours under an atmosphere of nitrogen. The xylene was evaporated under reduced pressure and the residual gum dissolved in diethyl ether and washed with aqueous sodium carbonate solution. The aqueous phase was re-extracted with diethyl ether (four times) and the combined organic phase dried (magnesium sulfate) and evaporated under reduced pressure to give an orange gum, which was fractionated by chromatography (silica, 15% methanol in dichloromethane) to give a yellow gum. The yellow gum was dissolved in aqueous hydrochloric acid (2M), extracted with ethyl acetate (three times), the acidic phase separated and basified with aqueous sodium carbonate solution. The aqueous basic phase was extracted with ethyl acetate (five times), the extracts combined, dried (magnesium sulfate) and evaporated under reduced pressure to give exo-3-(5-bromopyrid-3-yl)-endo-3-cyano-8-methyl-8-azabicyclo[3.2.1]oct-6-ene, 0.15 g, as a colourless solid, mp 106–8° C.

$^1$H NMR (CDCl$_3$): δ 2.20–2.35(7H,m); 3.65(2H,m); 6.25 (2H,s); 8.02(1H,t); 8.61(1H,d); 8.75(1H,d)ppm.

The following compounds were prepared using a similar procedure:

exo-3-(5-Chloropyrid-3-yl)-endo-3-cyano-8-methyl-8-azabicyclo[3.2.1]oct-6-ene (Compound No. 2 Table II), colourless solid; mp 107.0–108.5° C.; $^1$H NMR (CDCl$_3$): δ 2.20–2.40(4H,m); 2.30(3H,s); 3.65(2H,m); 6.25(2H,s); 7.90 (1H,t); 8.50(1H,d); 8.70(1H,d)ppm.

exo-3-(6-Chloropyrazin-2-yl)-endo-3-cyano-8-methyl-8-azabicyclo[3.2.1]oct-6-ene (Compound No. 3 Table II), colourless solid; mp 107.0–109° C.; $^1$H NMR (CDCl$_3$): δ 2.15(2H,dd); 2.30(3H,s); 2.55(2H,dd); 3.70(2H,m); 6.30 (2H,s); 8.55(1H,s); 8.80(1H,s)ppm.

EXAMPLE 7

This Example illustrates the preparation of endo-3-cyano-8-methyl-exo-3-(pyrid-3-yl)-8-azabicyclo[3.2.1]oct-6-ene (Compound No. 4 Table II).

Stage 1 exo-6-Hydroxy-8-methyl-8-azabicyclo[3.2.1]octan-3-one (1.0 g) was dissolved in dry 1,2-dimethoxyethane (25 ml) under an atmosphere of nitrogen with stirring, treated with 4-tolylsulfonylmethylisocyanide (1.64 g) and ethanol (0.62 ml) added. The mixture was cooled to 0° C. and potassium tert-butoxide (2.46 g) added in portions, keeping the reaction temperature below 10° C. The reaction was stirred at 0–5° C. for 2 hours, filtered and the insoluble material washed with 1,2-dimethoxyethane. The combined filtrate was evaporated under reduced pressure and the residue fractionated by chromatography (silica, 10% methanol by volume in dichloromethane) to give exo-3-cyano-exo-6-hydroxy-8-methyl-8-azabicyclo[3.2.1]-octane, 0.265 g, as a colourless solid, mp 120.0–121.5° C.

Stage 2

The product from Stage 1 (0.065 g) in dry tetrahydrofuran (2.0 ml) was treated with lithium diisopropylamide [prepared from n-butyl lithium (0.34 ml, hexane solution, 2.5M) and diisopropylamine (0.087 g)] in dry tetrahydrofuran (2.0 ml) under an atmosphere of nitrogen with stirring at –78° C. The mixture was stirred at –28° C. for 30 minutes, re-cooled to –78° C., a solution of 3-fluoropyridine (0.038 g) in dry tetrahydrofuran (1.0 ml) was added dropwise and the reaction was allowed to warm to ambient temperature over 18 hours. The reaction mixture was treated with water, extracted with dichloromethane (three times), the extracts combined, washed with saturated sodium chloride solution, dried (magnesium sulfate) and evaporated under reduced pressure. The residue was fractionated by chromatography (silica, 20% methanol by volume in dichloromethane) to give endo-3-cyano-exo-6-hydroxy-8-methyl-exo-3-(pyrid-3-yl)-8-azabicyclo[3.2.1]octane (Compound No. 7 Table III) as a colourless solid, 0.047 g, mp 123–125° C.

Stage 3

Diethylaminosulfur trifluoride (0.022 g) was dissolved in dry dichloromethane (0.5 ml) at 0° C. with stirring and endo-3-cyano-exo-6-hydroxy-8-methyl-exo-3-(pyrid-3-yl)-8-azabicyclo[3.2.1]octane (0.030 g) in dry dichloromethane (0.5 ml) was added dropwise. The mixture was stirred for 10 minutes at 0° C., allowed to warm to ambient temperature, re-cooled to 0° C., further diethylaminosulfur trifluoride (0.010 ml) added and the reaction allowed to warm to ambient temperature for 18 hours. The reaction mixture was treated with water, extracted with dichloromethane (three times), the combined organic phase washed with saturated sodium chloride solution, dried (magnesium sulfate) and evaporated under reduced pressure to give an oil. The oil was fractionated by chromatography (silica, 10% methanol by volume in dichloromethane) to give endo-3-cyano-8-methyl-exo-3-(pyrid-3-yl)-8-azabicyclo[3.2.1]oct-6-ene, 0.006 g, as a colourless solid, mp 64–65° C.

$^1$H NMR (CDCl$_3$): δ 2.20–2.40(4H,m); 2.30(3H,s); 3.65 (2H,m); 6.25(2H,s); 7.30(1H,dd); 7.90(1H,dt); 8.55(1H,dd); 8.82(1H,d)ppm.

EXAMPLE 8

This Example illustrates the preparation of exo-3-(5-bromopyrid-3-yl)-endo-3-cyano-exo-6-fluoro-8-methyl-8-azabicyclo[3.2.1]octane (Compound No. 8 Table III).

exo-3-(5-Bromopyrid-3-yl)-endo-3-cyano-exo-6-hydroxy-8-methyl-8-azabicyclo[3.2.1]octane (0.50 g) in anhydrous hydrogen fluoride (5 g) was cooled to –70° C. with stirring and sulfur tetrafluoride (2 g) added. The reaction mixture was stirred at –70° C. for 3 hours, warmed to ambient temperature allowing the volatiles to vent to waste and the pale yellow solution that remained was poured onto ice (100 g). The aqueous mixture was basified with aqueous sodium hydroxide (2M), extracted into dichloromethane (2×30 ml) and the combined organic phase re-extracted with hydrochloric acid (2×10 ml; 2M). The combined aqueous acidic phase was evaporated under reduced pressure to give a pale yellow solid, 0.52 g. The solid was treated with saturated aqueous sodium carbonate solution and extracted with ethyl acetate (three times). The combined extracts were dried (magnesium sulfate) and evaporated under reduced pressure to give a gum, 0.32 g, which was fractionated by chromatography (silica; 10% methanol in dichloromethane) to give the required product as a colourless solid, 0.11 g, mp 112–113° C.

$^1$H NMR (CDCl$_3$): δ 2.15–2.35(4H,m); 2.40–2.65(1H,m); 2.55(3H,t); 2.85–3.00(1H,m); 3.50–3.70(2H,m); 5.20 and 5.90(1H, two m); 7.99(1H,t); 8.65(1H,d); 8.75(1H,d)ppm.

EXAMPLE 9

This Example illustrates the preparation of exo-3-(5-bromopyrid-3-yl)-endo-3-cyano-8-methyl-8-azabicyclo [3.2.1]octan-6-one (Compound No. 9 Table III).

To a stirred solution of dimethyl sulfoxide (0.33 ml, dry) in dry dichloromethane (2 ml) under an atmosphere of nitrogen at –78° C. was added dropwise oxalyl chloride (0.23 ml), maintaining the reaction temperature below –60° C. The mixture was stirred for 0.25 hour and a solution of exo-3-(5-bromopyrid-3-yl)-endo-3-cyano-exo-6-hydroxy-8-methyl-8-azabicyclo[3.2.1]octane (0.50 g) in dry dichloromethane (8 ml) was added dropwise at –60° C. and stirred for 2 hours. Triethylamine (0.87 ml, dry) was then added dropwise, the reaction stirred for 0.25 hour at –60° C. and allowed to slowly warm to ambient temperature for 2 days.

The mixture was poured into water, extracted with dichloromethane (three times), the combined organic phase dried (magnesium sulfate) and evaporated under reduced pressure to give an orange gum, 0.40 g. The gum was fractionated by chromatography (silica; 10% methanol in dichloromethane) to give the required product as an off-white solid, 0.23 g, mp 147–149° C.

$^1$H NMR (CDCl$_3$): δ 2.35–2.65(7H,m); 2.70–2.95(2H,m); 3.15(1H,m); 3,75(1H,m); 8.00(1H,t); 8.68(1H,d); 8.75(1H,d)ppm.

EXAMPLE 10

This Example illustrates the preparation of exo-3-(5-bromopyrid-3-yl)-endo-3-cyano-6,6-difluoro-8-methyl-8-azabicyclo[3.2.1]octane (Compound No. 10 Table III).

exo-3-(5-Bromopyrid-3-yl)-endo-3-cyano-8-methyl-8-azabicyclo[3.2.1]octan-6-one (0.50 g) was dissolved in diethylaminosulfurtrifluoride (5.0 ml) at ambient temperature with stirring under an atmosphere of nitrogen. The solution was warmed to 30° C. for 6 hours and stored at ambient temperature for 18 hours. The reaction mixture was added dropwise to ice, neutralised with aqueous sodium carbonate solution, extracted with ethyl acetate (three times), dried (magnesium sulfate) and evaporated under reduced pressure to give the required product as an off-white solid, 0.33 g. The solid was further fractionated by chromatography (silica; 5% methanol in dichloromethane) to give the required product as a colourless solid, 0.268 g.

$^1$H NMR (CDCl$_3$): δ 2.20–2.35(2H,m); 2.40–2.60(5H,m); 2.70–3.00(2H,m); 3.30(1H,m); 3.60(1H,m); 8.05(1H,t); 8.65(1H,d); 8.80(1H,d)ppm.

EXAMPLE 11

This Example illustrates the preparation of exo-3-(5-chloropyrid-3-yl)-endo-3-cyano-8-benzyl-8-azabicyclo[3.2.1]oct-6-ene (Compound No. 5 Table II).

Stage 1

2,5-Dimethoxy-2,5-dihydrofuran (97.5 g) was dissolved in water (650 ml) and treated with aqueous hydrochloric acid (3.75 ml, 2M) under an atmosphere of nitrogen. The mixture was heated to 96° C. with stirring and aqueous methanol (about 100 ml) distilled from the reaction vessel until the reaction solution reached 98–99° C. The reaction was cooled to ambient temperature, acetone dicarboxylic acid (146 g) added in one portion followed by a solution of sodium hydrogen phosphate (53.25 g) and sodium hydroxide (15.0 g) in water (500 ml). 1,4-Dioxane (100 ml) was added and a solution of benzylamine hydrochloride (71.75 g) in water (330 ml) added dropwise over 10 minutes. The mixture was rapidly stirred for a further 4 hours, acidified with aqueous hydrochloric acid (2M), dichloromethane (500 ml) added and the reaction mixture stirred for 10 minutes. The aqueous phase was decanted from the residual brown gum, filtered through a bed of kieselguhr and the filtrate extracted with dichloromethane (3×500 ml). The aqueous phase was collected, basified with potassium carbonate and extracted with ethyl acetate (3×1000 ml). The organic fractions were combined, dried (magnesium sulfate) and evaporated under reduced pressure to give a brown oil, 55 g, containing a mixture of exo- and endo-6-hydroxy-8-benzyl-8-azabicyclo[3.2.1]octan-3-one (ratio 7:1).

Stage 2 tert-Butyldimethylsilyl chloride (26.5 g) was dissolved in N,N-dimethylformamide (400 ml, dry) with stirring under an atmosphere of nitrogen and imidazole (25.0 g) added in portions. The mixture was stirred for 10 minutes and a solution of the product from Stage 1 (55 g) in N,N-dimethylformamide (250 ml, dry) added in portions. The dark brown reaction mixture was stirred at ambient temperature for 3 hours, stored for 18 hours and poured into water (2,500 ml). The product was extracted into hexane (3×800 ml), the combined organic phases washed with water (2×1000 ml) and dried (sodium sulfate). The solvent was evaporated under reduced pressure to give a brown oil, 44.5 g, containing a mixture of exo- and endo-6-tert-butyldimethylsilyloxy-8-benzyl-8-azabicyclo[3.2.1]octan-3-one (ratio 7:1).

Stage 3

The material from Stage 2 (44 g) in 1,2-dimethoxyethane (160 ml, dry) containing 4-tolylsulfonylmethylisocyanide (41 g) was added dropwise over 1.5 hours to a mixture of potassium tert-butoxide (19.0 g) and sodium ethoxide (14.5 g) in 1,2-dimethoxyethane (140 ml, dry) at 40° C. under an atmosphere of nitrogen. The mixture was stirred for 1 hour at 40° C. and allowed to cool to ambient temperature and stirred for a further 18 hour. The mixture was poured into water (1,500 ml), extracted with hexane (2×750 ml), and the combined organic phases washed with water (400 ml) and dried (sodium sulfate). The solvent was evaporated under reduced pressure to give a brown gum, 39.7 g, containing a mixture of exo- and endo-6-tert-butyldimethylsilyloxy-8-benzyl-exo-3-cyano-8-azabicyclo[3.2.1]octane (ratio 7:1).

Stage 4

The product from Stage 3 (15.0 g) was dissolved in dry tetrahydrofuran (100 ml) containing 3,5-dichloropyridine (4.30 g) at 0° C. under an atmosphere of nitrogen with stirring. Lithium bis-(trimethylsilyl) amide (38.0 ml of a tetrahydrofuran solution, 1M) was added dropwise to the solution over 1 hour, maintaining the reaction temperature below 5° C. The reaction was allowed to warm to ambient temperature and stirred for 18 hours. The reaction mixture was treated with further lithium bis-(trimethylsilyl) amide (7.0 ml of a tetrahydrofuran solution, 1M) added dropwise over 2 hours at ambient temperature, stirred for 6 hours and stored for 18 hours. The mixture was poured into water (500 ml), extracted with hexane (2×400 ml), the combined organic phase was washed with water, dried (sodium sulfate) and evaporated under reduced pressure to give a brown oil, 18.5 g. The oil was fractionated by chromatography (silica, hexane/ethyl acetate 10:1 by volume) to give 8-benzyl-exo-6-tert-butyldimethylsilyloxy-exo-3-(5-chloropyrid-3-yl)-endo-3-cyano-8-azabicyclo[3.2.1]octane (Compound No. 11 Table III), yellow oil, 7.8 g.

$^1$H NMR (CDCl$_3$): δ 0.15(6H,two s); 0.90(9H,s); 2.19–2.40(5H,m); 2.80–2.90(1H,q); 3.30(1H,m); 3.60(1H,m); 3.90–4.10(2H,q); 5.05(1H,dd); 7.20–7.45(5H,m); 7.80 (1H,t); 8.55(1H,d); 8.70(1H,d)ppm.

Stage 5

The product from Stage 4 (4.92 g) was dissolved in tetrahydrofuran (20 ml) with stirring, aqueous hydrochloric acid (30 ml, 4M) added and the mixture stirred at ambient temperature for 18 hours and stored for 3 days. The mixture was diluted with water, extracted with ethyl acetate (three times) and the acidic aqueous phase separated and basified with sodium carbonate. The aqueous basic phase was extracted with dichloromethane (three lo times), dried (magnesium sulfate) and evaporated under reduced pressure to give exo-3-(5-chloropyrid-3-yl)-endo-3-cyano-exo-6-hydroxy-8-benzyl-8-azabicyclo[3.2.1]octane (Compound No. 12 Table III) as an off-white solid, 2.71 g, mp 162.5–164.5° C.

$^1$H NMR (CDCl$_3$): δ 2.00(1H,d); 2.10–2.40(4H,m); 2.95 (1H,q); 3.40(1H,m); 3.60(1H,m); 4.00(2H,q); 5.05(1H,m); 7.20–7.40(5H,m); 7.85(1H,t); 8.55(1H,d); 8.70(1H,d)ppm.

Stage 6

The product from Stage 5 (2.61 g) was suspended in dichloromethane (30 ml) containing 4-dimethylaminopyridine (0.99 g) with stirring at ambient temperature. 4-Tolyl chlorothionoformate (1.25 ml) was added dropwise and the reaction mixture stirred at ambient temperature for 18 hours. The mixture was poured into water, extracted with dichloromethane (three times), the combined organic phase dried (magnesium sulfate) and evaporated under reduced pressure to give a brown oil containing exo-3-(5-chloropyrid-3-yl)-endo-3-cyano-exo-6-(thiono-4-tolyloxy)-8-benzyl-8-azabicyclo[3.2.1]octane, which was used in Stage 7 without further purification.

Stage 7

The product from Stage 6 (4.5 g) was dissolved in xylene (40 ml, dry) and heated to 160° C. for 18 hours under an atmosphere of nitrogen with stirring. The reaction was cooled to ambient temperature, treated with aqueous hydrochloric acid (2M) until strongly acidic and extracted with ethyl acetate (three times). The aqueous acidic phase was separated, basified with sodium carbonate, extracted with ethyl acetate (three times) and the organic phases combined and dried (magnesium sulfate). The solvent was evaporated under reduced pressure to give the required product as an off-white solid, 2.20 g. A portion, (0.2 g), was fractionated by thick layer chromatography (silica; hexane/ethyl acetate 1:1 by volume) to give an analytically pure sample of the required product, (0.15 g), colourless solid, mp 130–1° C.

$^1$H NMR (CDCl$_3$): δ 2.20–2.40(4H,m); 3.60(2H,s); 3.75 (2H,m); 6.30(2H,s); 7.20–7.40(5H,m); 7.85(1H,t); 8.55(1H, d); 8.75(1H,d)ppm.

EXAMPLE 12

This Example illustrates the preparation of exo-3-(5-chloropyrid-3-yl)-endo-3-cyano-8-azabicyclo[3.2.1]oct-6-ene (Compound No. 6 Table II).

The product from Example 11, Stage 7 (2.0 g) was dissolved in monofluorobenzene (20 ml, dry) containing diethyl azodicarboxylate (1.5 ml) and the mixture heated to reflux with stirring for 5 days. Further diethyl azodicarboxylate (1.5 ml) was added, the reaction heated for an additional 2 days and stored at ambient temperature for 18 hours. The volatiles were evaporated under reduced pressure to give an orange-brown gum which was dissolved in ethanol (20 ml) containing aqueous hydrochloric acid (20 ml, 2M). The solution was heated to reflux with stirring for 7 hours, allowed to cool to ambient temperature and stored for 18 hours. The reaction mixture was diluted with water, extracted with ethyl acetate (three times), and the aqueous acidic phase separated and basified with sodium carbonate. The aqueous basic phase was extracted with ethyl acetate (three times), dried (magnesium sulfate) and evaporated under reduced pressure to give an orange oil. The oil was fractionated by eluting through a short column of silica with hexane/ethyl acetate (1:1 by volume) to remove by-products and dichloromethane/methanol (10:1 by volume) to give the required product (0.7 g), colourless solid, mp 94.5–95.5° C. A sample was further fractionated by preparative thick layer chromatography (silica; 20% methanol/dichloromethane) to provide an analytically pure sample, mp 98–100° C.

$^1$H NMR (CDCl$_3$): δ 2.15–2.40(4H,m); 4.10(2H,m); 6.50 (2H,m); 7.85(1H,t); 8.55(1H,d); 8.70(1H,d)ppm.

EXAMPLE 13

This Example illustrates the preparation of exo-3-(5-chloropyrid-3-yl)-endo-3-cyano-8-(2,2-difluoroethyl)-8-azabicyclo[3.2.1]oct-6-ene (Compound No. 7 Table II).

The product from Example 11, Stage 7 (0.19 g) was dissolved in N,N-dimethylformamide (0.4 ml, dry) containing potassium carbonate (0.16 g), potassium iodide (0.026 g) and 1-bromo-2,2-difluoroethane (0.157 g). The mixture was stirred and heated to 50° C. in a sealed glass vessel for 3 days, cooled to ambient temperature and poured into water. The mixture was extracted with diethyl ether (four times), the combined organic phases washed with aqueous sodium chloride solution, dried (magnesium sulfate) and evaporated under reduced pressure to give a colourless solid. The solid was fractionated by preparative thick layer chromatography (basic alumina; diethyl ether) to give the required product as a colourless solid, 0.114 g, mp 120.0–121.5° C.

$^1$H NMR (CDCl$_3$): δ 2.20–2.40(4H,m); 2.65–2.80(2H,dt); 3.85(2H,m); 5.70–6.10(1H,tt); 6.30(2H,s); 7.85(1H,t); 8.55 (1H,d); 8.70(1H,d)ppm.

EXAMPLE 14

This Example illustrates the preparation of exo-3-(5-bromopyrid-3-yl)-endo-3-cyano-8-(vinyloxycarbonyl)-8-azabicyclo[3.2.1]oct-6-ene (Compound No. 8 Table II).

Vinyl chloroformate (0.1 ml, stored over anhydrous potassium carbonate) was added to 1,2-dichloroethane (10 ml, dry) and half the volume of solvent distilled to remove any residual hydrogen chloride present in the chloroformate. To the solution at ambient temperature was added the product from Example 6, Stage 6 (0.100 g) and the mixture stirred for 1 hour and then heated to reflux for 48 hours. Further vinyl chloroformate (0.1 ml) was added to the reaction mixture which was heated for an additional 48 hours, the reaction cooled to ambient temperature and poured into saturated aqueous ammonium chloride solution. The product was extracted into ethyl acetate (three times) and the combined extracts backwashed with ammonium chloride solution, dried (magnesium sulfate) and evaporated under reduced pressure to give a yellow oil. The oil was fractionated by preparative thick layer chromatography (silica; hexane/ethyl acetate 1:1 by volume) to give the required product as a pale yellow oil, 0.057 g.

$^1$H NMR (CDCl$_3$): δ 2.20–2.45(4H,m); 4.55(1H,dd); 4.85 (1H,dd); 4.95(2H,m); 6.45(2H,brd); 7.25(1H,t); 7.90 (1H,t); 8.62(2H,two d)ppm.

EXAMPLE 15

This Example illustrates the preparation of exo-3-(5-bromopyrid-3-yl)-endo-3-cyano-8-azabicyclo[3.2.1]oct-6-ene (Compound No. 9 Table II).

The product from Example 6, Stage 6 (0.150 g) was dissolved in fluorobenzene (2 ml, dry) containing diethyl azodicarboxylate (0.12 ml) and heated to reflux with stirring for 18 hours. The reaction was cooled to ambient temperature, evaporated under reduced pressure, the residual yellow oil dissolved in ethanol (2 ml) containing aqueous hydrochloric acid (2 ml, 2M) and heated to reflux for 4 hours and allowed to cool to ambient temperature. The mixture was poured into dilute hydrochloric acid and extracted with dichloromethane (three times) and the aqueous acidic phase basified with sodium carbonate. The basic aqueous phase was extracted with dichloromethane (three times), the combined extracts washed with aqueous sodium chloride solution, dried (magnesium sulfate) and evaporated under reduced pressure to give a yellow gum. The gum was fractionated by preparative thick layer chromatography (silica; 20% methanol/dichloromethane) to give the required product as a colourless solid, 0.078 g, mp 150–151° C.

$^1$H NMR (CDCl$_3$): δ 2.15–2.35(4H,m); 4.10(2H,m); 6.50 (2H,s); 8.05(1H,t); 8.62(1H,d); 8.78(1H,d)ppm.

EXAMPLE 16

This example illustrates the preparation of 8-allyl-exo-3-(5-bromopyrid-3-yl)-endo-3-cyano-8-azabicyclo[3.2.1]oct-6-ene (Compound No. 10 Table II).

The product from Example 15 (0.200 g) was dissolved in ethanol (5 ml, dry) containing anhydrous potassium carbonate (0.095 g) and allyl bromide (0.1 ml). The mixture was stirred and heated to reflux for 7 hours and allowed to cool to ambient temperature for 18 hours. The insoluble inorganic material was removed by filtration and the filtrate evaporated under reduced pressure to give a yellow oil which was fractionated by preparative thick layer chromatography (silica; 5% methanol/dichloromethane) to give the required product as an off-white solid, 0.123 g, mp 84.5–85.5° C.

$^1$H NMR (CDCl$_3$): δ 2.25(4H,m); 3.00(2H,d); 3.80(2H,m); 5.20(2H,m); 5.80–5.95(1H,m); 6.25(2H,s); 8.00(1H,t); 8.60(1H,d); 8.75(1H,d)ppm.

EXAMPLE 17

This Example illustrates the preparation of exo-3-(5-bromopyrid-3-yl)-endo-3-cyano-8-(2,2,2-trifluoroethyl)-8-azabicyclo[3.2.1]oct-6-ene (Compound No. 11 Table II).

2,2,2-Trifluoroethanol (0.050 ml) was dissolved in dichloromethane (2 ml, dry) containing N,N-diisopropylethylamine (0.13 ml) and cooled to −78° C. with stirring under an atmosphere of nitrogen. Trifluoromethanesulfonic anhydride (0.13 g) was added drowise to the mixture, which was stirred at −78° C. for 0.5 hour, then allowed to warm to ambient temperature and stirred for a further 1 hour. The product from Example 15 (0.200 g) was dissolved in dichloromethane (2 ml, dry) containing N,N-diisopropylethylamine (0.13 ml) and the mixture added to the solution of 2,2,2-trifluoroethyl trifluoromethanesulfonate made earlier. The reaction mixture was stirred at ambient temperature for 4 hours and stored for 18 hours.

Further 2,2,2-trifluoroethyl trifluoromethanesulfonate was prepared as described previously [from trifluoroethanol (0.1 ml), trifluoromethanesulfonic anhydride (0.26 ml) and N,N-diisopropylethylamine (0.13 ml) in dichloromethane (2 ml)] and added to the reaction, which was stirred at ambient temperature for an additional 5 hours. The mixture was poured into a saturated solution of aqueous sodium carbonate, extracted with ethyl acetate (three times). The combined organic phase was dried (magnesium sulfate) and evaporated under reduced pressure to give an orange solid. The solid was fractionated by preparative thick layer chromatography (silica; hexane:ethyl acetate 1:1 by volume) to give the required product as a colourless solid, 0.050 g, mp 128–130° C.

$^1$H NMR (CDCl$_3$): δ 2.20–2.40(4H,m); 2.90(2H,q); 3.90 (2H,m); 6.35(2H,s); 7.95(1H,t); 8.65(1H,d); 8.75(1H,d) ppm.

The following compounds were prepared using a similar procedure from the appropriate amine:

exo-3-(5-Bromopyrid-3-yl)-endo-3-cyano-8-(2-methylpentyl)-8-azabicyclo[3.2.1]oct-6-ene (Compound No. 12 Table II), orange gum; $^1$H NMR (CDCl$_3$): δ 0.85–0.95(6H,m); 1.25–1.55(5H,m); 2.05(1H,m); 2.20–2.35 (5H,m); 3.70(2H,m); 6.25(2H,q); 8.00(1H,t); 8.60(1H,d); 8.70(1H,d)ppm was prepared from 2-methylpentanol.

exo-3-(5-Chloropyrid-3-yl)-endo-3-cyano-8-(2,2,2-trifluoroethyl)-8-azabicyclo[3.2.1]oct-6-ene (Compound No. 13 Table II), colourless solid; mp 117–120° C.; $^1$H NMR (CDCl$_3$): δ 2.25–2.40(4H,m); 2.90(2H,q); 3.85(2H,m); 6.35 (2H,s); 7.50(1H,t); 8.55(1H,d); 8.75(1H,d)ppm was prepared from 2,2,2-trifluoroethanol.

exo-3-(5-Chloropyrid-3-yl)-endo-3-cyano-8-(2-methylpropyl)-8-azabicyclo[3.2.1]oct-6-ene (Compound No. 14 Table II), colourless oil; $^1$H NMR (CDCl$_3$): δ 0.95(6H,d); 1.65(1H,m); 2.10–2.35(6H,m); 3.70(2H,m); 6.25(2H,s); 7.85(1H,t); 8.55(1H,d); 8.70(1H,d)ppm was prepared from 2-methylpropan-1-ol.

EXAMPLE 18

This Example illustrates the preparation of exo-3-(5-chloropyrid-3-yl)-endo-3-cyano-8-(ethoxycarbonyl)-8-azabicyclo[3.2.1]oct-6-ene (Compound No. 15 Table II).

Ethyl chloroformate (0.040 ml) was added to the product from Example 12, Stage 7 (0.10 g) dissolved in dichloromethane (2 ml, dry) containing N,N-diisopropylethylamine (0.078 ml) and the mixture stirred at ambient temperature for 2 hours. The mixture was poured into a solution of aqueous sodium carbonate (20 ml), extracted with ethyl acetate (2×20 ml). The organic extracts were combined, dried (magnesium sulfate) and evaporated under reduced pressure to give the required product as a colourless oil, 0.122 g.

$^1$H NMR (CDCl$_3$): δ 1.20(3H,t); 2.20–2.45(4H,m); 4.25 (2H,q); 4.85(2H,m); 6.45(2H,m); 7.75(1H,t); 8.50(1H,d); 8.55(1H,d)ppm.

EXAMPLE 19

This Example illustrates the preparation of exo-3-(5-chloropyrid-3-yl)-endo-3-cyano-8-(3,3,3-trifluoropropyl)-8-azabicyclo[3.2.1]oct-6-ene (Compound No. 16 Table II).

The product from Example 11, Stage 7 (0.21 g) was dissolved in N,N-diethylformamide (3 ml, dry) containing potassium iodide (0.02 g, catalyst) and 1-bromo-3,3,3-trifluoropropane (0.090 ml). The mixture was heated to 80° C. with stirring for 24 hours, further 1-bromo-3,3,3-trifluoropropane (0.040 ml) added and the mixture heated for an additional 3 hours at 90° C. The reaction was cooled to ambient temperature, stored for 18 hours and the solvent evaporated under reduced pressure. The residue was treated with a solution of aqueous sodium hydrogen carbonate (10 ml) and extracted with ethyl acetate (2×10 ml), dried (magnesium sulfate) and evaporated under reduced pressure to give a gum. The gum was fractionated by preparative thick layer chromatography (basic alumina; diethyl ether) to give the required product as a colourless waxy solid 0.096 g, (no distinct mp, softened 70–80° C.).

$^1$H NMR (CDCl$_3$): δ 2.20–2.40(6H,m); 2.65(2H,t); 3.75 (2H,m); 6.30(2H,s); 7.85(1H,t); 8.55(1H,d); 8.70 (1H,d) ppm.

EXAMPLE 20

This Example illustrates the preparation of exo-3-(5-chloropyrid-3-yl)-endo-3-cyano-8(prop-2-yn-1-yl)-8-azabicyclo[3.2.1]oct-6-ene (Compound No. 17 Table II).

The product from Example 11, Stage 7 (1.00 g) was dissolved in propan-2-ol (10 ml, dry) containing anhydrous potassium carbonate (1.00 g) and propargyl chloride (0.50 ml). The mixture was heated to reflux for 10 hours with stirring, allowed to cool to ambient temperature then was stored for 18 hours. The solvent was evaporated under reduced pressure, the residue extracted into ethyl acetate (20 ml) and the extract was washed with aqueous sodium carbonate solution (2×20 ml), dried (magnesium sulfate) and evaporated under reduced pressure to give a brown gum. The gum was fractionated by preparative thick layer chromatography (basic alumina; hexane:ethyl acetate, 4:1 by volume) to give the required product as a solid, 0.072 g, mp 124–127° C.

$^1$H NMR (CDCl$_3$): δ 2.20–2.40(5H,m); 3.20(2H,d); 3.95 (2H,m); 6.25(2H,s); 7.90(1H,t); 8.55(1H,d); 8.70(1H,d) ppm.

EXAMPLE 21

This Example illustrates the preparation of 8-(but-2-yn-4-yl)-exo-3-(5-chloropyrid-3-yl)-endo-3-cyano-8-azabicyclo[3.2.1]oct-6-ene (Compound No. 18 Table II).

The product from Example 11, Stage 7 (0.200 g) was dissolved in tetrahydrofuran (2 ml, dry) containing N,N-diisopropylethylamine (0.14 ml) and but-2-yn-1-yl 4-tolylsulfonate (0.182 g). The mixture was stirred and heated to reflux for 2 hours, cooled to ambient temperature, poured into water and extracted with diethyl ether (three times). The combined organic phase was dried (magnesium sulfate), evaporated under reduced pressure and the residual yellow gum fractionated by preparative thick layer chromatography (silica; hexane:ethyl acetate 1:1 by volume) to give the required product as a colourless solid, 0.073 g, mp 132–3° C.

$^1$H NMR (CDCl$_3$): δ 1.85(3H,t); 2.20–2.40(4H,m); 3.15 (2H,m); 3.95(2H,m); 6.25(2H,s); 7.90(1H,t); 8.55(1H,d); 8.75(1H,d)ppm.

EXAMPLE 22

This Example illustrates the preparation of exo-3-(5-chloropyrid-3-yl)-endo-3-cyano-8-(2-cyanoethyl)-8-azabicyclo[3.2.1]oct-6-ene (Compound No. 19 Table II).

The product from Example 11, Stage 7 (0.200 g) was dissolved in N,N-dimethylformamide (3 ml, dry) containing N,N-diisopropylethylamine (0.16 ml) and 1-bromo-2-cyanoethane (0.074 ml). The mixture was stirred and heated to 100° C. for 18 hours, the mixture was cooled to ambient temperature, poured into water, extracted with diethyl ether (three times), the combined extracts were washed with water, dried (magnesium sulfate) and evaporated under reduced pressure to give a brown oil. The oil was fractionated by preparative thick layer chromatography (silica; hexane:ethyl acetate 1:1 by volume) to give the required product as a pale yellow oil, 0.095 g.

$^1$H NMR (CDCl$_3$): δ 2.20–2.40(4H,m); 2.50(2H,t); 2.70 (2H,t); 3.85(2H,m); 6.35(2H,s); 7.85(1H,t); 8.55(1H,d); 8.70(1H,d)ppm.

EXAMPLE 23

This Example illustrates the preparation of exo-3-(5-chloropyrid-3-yl)-endo-3-cyano-8-(methyl propion-2-yl)-8-azabicyclo[3.2.1]oct-6-ene (Compound No. 20 Table II) and 8-[carbonyloxy(methyl propion-2-yl)]-exo-3-(5-chloropyrid-3-yl)-endo-3-cyano-8-azabicyclo[3.2.1]oct-6-ene (Compound No. 21 Table II).

The product from Example 11, Stage 7 (0.195 g) was dissolved in N-methylpyrrolidin-2-one (2 ml, dry) containing methyl (S)(–) 2-chloropropionate (0.17 ml) and potassium carbonate (0.164 g, anhydrous). The mixture was heated in a sealed glass vessel at 100° C. for 24 hours, cooled to ambient temperature and poured into water. The aqueous mixture was extracted with ethyl acetate (three times), the combined extracts were washed with an aqueous solution of sodium chloride, dried (magnesium sulfate) and evaporated under reduced pressure to give a brown oil. The oil was fractionated by thick layer chromatography (silica; ethyl acetate) to give a yellow oil, 0.050 g, which was further fractionated by HPLC (Partisil 5, hexane:ethyl acetate 1:1 by volume) to give:

exo-3-(5-Chloropyrid-3-yl)-endo-3-cyano-8(methyl propion-2-yl)-8-azabicyclo[3.2.1]oct-6-ene, 0.022 g as a colourless oil; $^1$H NMR (CDCl$_3$): δ 1.30(3H,d); 2.20–2.40 (4H,m); 3.30(1H,q); 3.70(3H,s); 3.90(1H,m); 4.05(1H,m); 6.30(2H,m); 7.85(1H,t); 8.55(1H,d); 8.70(1H,d)ppm; and, 8-[Carbonyloxy(methyl propion-2-yl)]-exo-3-(5-chloropyrid-3-yl)-endo-3-cyano-8-azabicyclo[3.2.1]oct-6-ene, 0.085 g, as a colourless gum; $^1$H NMR (CDCl$_3$): δ 0.085 g 1.55(3H,m); 2.10–2.20(2H,m); 2.40(1H,dd); 2.70 (1H,dd); 3.85(3H,s); 4.80(1H,m); 4.90(1H,m); 5.20 (1H,q); 6.45(2H,m); 8.10(1H,t); 8.55(1H,d); 8.80(1H,d)ppm.

EXAMPLE 24

This Example illustrates the preparation of exo-3-(5-chloropyrid-3-yl)-endo-3-cyano-8-(methoxy)-8-azabicyclo [3.2.1]oct-6-ene (Compound No. 22 Table II).

Stage 1

The product from Example 11, Stage 7 (0.600 g) was added to a stirred suspension of disodium hydrogen phosphate (1.735 g) in tetrahydrofuran (5 ml) at ambient temperature. Benzoyl peroxide (0.929 g) in tetrahydrofuran (10 ml) was added dropwise and the mixture stirred for 6 days at ambient temperature. The mixture was poured into aqueous sodium metabisulfite solution, basified with sodium carbonate and extracted into ethyl acetate (four times). The combined organic phase was dried (magnesium sulfate) and evaporated under reduced pressure to give a pale yellow oil. The oil was fractionated by chromatography (silica; 10–50% ethyl acetate in hexane) to give 8-(benzoyloxy)-exo-3-(5-chloropyrid-3-yl)-endo-3-cyano-8-azabicyclo[3.2.1]oct-6-ene (Compound No. 23 Table II) as a colourless solid, 0.625 g, mp 140.5–141.5° C.

$^1$H NMR (CDCl$_3$): δ 2.15 and 2.45(2H,two m); 2.60 and 2.75(2H,two dd,); 4.45 and 4.50(2H,two m); 6.40 and 6.50 (2H,two m); 7.40–7.70(3H,m);7.90–8.10(3H,m); 8.60(1H, d); 8.80(1H,d)ppm, consistent with a 6:1 mixture of equatorial and axial N-substituted isomers.

Stage 2

The product from Stage 1 (0.525 g) was added to a solution of potassium hydroxide (0.121 g) in methanol (5 ml) at ambient temperature and stirred for 2 hours, and stored for 18 hours. The mixture was diluted with a small volume of water, and extracted with ethyl acetate (three times), the combined extracts dried (magnesium sulfate) and evaporated under reduced pressure to give a colourless solid. The solid was extracted with hot hexane to remove minor impurities and the insoluble exo-3-(5-chloropyrid-3-yl)-endo-3-cyano-8-hydroxy-8-azabicyclo [3.2.1]oct-6-ene (Compound No. 24 Table II), 0.250 g, collected by filtration.

$^1$H NMR (CDCl$_3$): δ 1.85(d), 2.35–2.50(two dd), 2.70 (dd), total of 4H; 3.85(m) and 4.18(m), total of 2H; 6.32 and 6.36(two s), total of 2H; 7.85 and 8.02(two t) total of 1H; 8.54(d,1H); 8.68 and 8.86(two d)ppm, total of 1H; consistent with a 3:1 mixture of N-hydroxy axial and equatorial isomers.

Stage 3

The product from Stage 2 (0.200 g) in N,N-dimethylformamide (3 ml, dry) was added dropwise to a stirred suspension of sodium hydride (0.031 g, 60% dispersion in mineral oil) in N,N-dimethylformamide (2 ml, dry) at –10° C. under an atmosphere of nitrogen. The orange solution was stirred for 0.25 hours, methyl iodide (0.048 ml) added and the mixture stirred at 0° C. for 4 hours and stored at 5° C. for 5 days. The mixture was diluted with water and extracted with diethyl ether (three times). The combined extracts were washed with an aqueous solution of sodium chloride, dried (magnesium sulfate) and evaporated under reduced pressure to give a yellow oil. The oil was fractionated by preparative thick layer chromatography (silica; ethyl acetate) to give the required product as a yellow gum, 0.025 g.

$^1$H NMR (CDCl$_3$): δ 1.90(dd),2.30–2.60(m), total of 4H; 3.55 and 3.65 (two s), total of 3H; 4.05 and 4.25(two m), total of 2H; 6.30 and 6.35(one s, one dd), total of 2H; 7.85 and 7.95(two t)total of 1H; 8.55(1H,d); 8.70 and 8.80(two d)ppm, total of 1H; consistent with a 1:1 mixture of axial and equatorial N-substituted isomers.

EXAMPLE 25

This Example illustrates the preparation of exo-3-(6-methoxypyrazin-2-yl)-endo-3-cyano-8-methyl-8-azabicyclo[3.2.1]oct-6-ene (Compound No. 25 Table II).

exo-3-(6-Chloropyrazin-2-yl)-endo-3-cyano-8-methyl-8-azabicyclo[3.2.1]oct-6-ene (0.303 g) was dissolved in methanol (10 ml) and treated with sodium methoxide with stirring under an atmosphere of nitrogen. The mixture was heated to reflux for 24 hours, cooled to ambient temperature and stored for 1 day. The solvent was evaporated under reduced pressure and the residue extracted into diethyl ether and filtered to remove the inorganic material. The filtrate was evaporated under reduced pressure to give the required product as a colourless solid, 0.28 g, mp 92–4° C.

$^1$H NMR (CDCl$_3$): δ 2.20(2H,dd); 2.30(3H,s); 2.50(2H, dd); 3.65(2H,m); 4.00(3H,s); 6.28(2H,s); 8.15(1H,s); 8.40 (1H,s)ppm.

EXAMPLE 26

This Example illustrates the preparation of 8-benzyl-exo-3-(5-chloropyridyl)-6-exo-cyano-8-azabicyclo[3.2.1]octane (Compound No. 13 Table III) and 8-benzyl-exo-3-(5-chloropyridyl)-6-endo-cyano-8-azabicyclo[3.2.1]octane (Compound No. 14 Table III).

Stage 1

8-Benzyl-exo-6-tert-butyldimethylsilyloxy-exo-3-(5-chloropyrid-3-yl)-3-endo-cyano-8-azabicyclo[3.2.1]octane (Compound No. 11 Table III; 4.90 g) was dissolved in tetrahydrofuran (dry, 60 ml) and cooled to 0° C. with stirring under an inert atmosphere of nitrogen. Lithium aluminium hydride (21.0 ml of a solution in tetrahydrofuran, 1M) was added dropwise over 30 minutes, the mixture stirred for a further 1 hour at 0° C. and allowed to warm to ambient temperature. The reaction was stored for 30 hours, quenched with, in order of addition, water (0.76 ml), sodium hydroxide solution (0.76 ml, 2M) and further water (1.52 ml). The resulting mixture was filtered through a bed of kieselguhr and the filtrate partioned between water and ethyl acetate. The aqueous fraction was separated, re-extracted with ethyl acetate (three times) and the combined organic phase dried (magnesium sulfate) and evaporated under reduced pressure to give a brown gum, 3.23 g, containing 8-benzyl-exo-6-tert-butyldimethylsilyloxy-exo-3-(5-chloropyrid-3-yl)-8-azabicyclo[3.2.1]octane (Compound No. 15 Table III).

Stage 2

The product from Stage 1 (3.23 g) was dissolved in tetrahydrofuran (25 ml) with stirring and hydrochloric acid (50 ml, 4M) added. The reaction was stirred for 1 hour at ambient temperature and stored for 18 hours. The mixture was diluted with water, washed with ethyl acetate (twice) and the aqueous fraction basified with aqueous sodium carbonate solution and extracted with dichloromethane (three times). The dichloromethane extracts were combined, washed with water, dried (magnesium sulfate) and evaporated under reduced pressure to give a gum, 1.34 g. The gum was extracted with hot ethyl acetate, filtered and re-evaporated under reduced pressure to give a gum, 1.15 g, containing 8-benzyl-exo-3-(5-chloropyrid-3-yl)-exo-6-hydroxy-8-azabicyclo[3.2.1]octane (Compound No. 16 Table III).

Stage 3

Dimethyl sulfoxide (dry, 0.52 ml) was dissolved in dichloromethane (dry, 2 ml) and cooled to –75° C. under an atmosphere of nitrogen with stirring. Oxalyl chloride (0.23 ml) was added dropwise, maintaining the reaction below –60° C. The mixture was stirred at –75° C. for 30 minutes and the product from Stage 2 (0.500 g) in dichloromethane (8 ml) was added dropwise, maintaining the reaction below –60° C. On complete addition the reaction was stirred at –75° C. for 2 hours, triethylamine (dry, 0.85 ml) was added dropwise, stirred for an additional 15 minutes at –75° C. and allowed to warm to ambient temperature. The mixture was stored for 18 hours, quenched with water, extracted with ethyl acetate (three times) and the combined organic phase dried (magnesium sulfate) then evaporated under reduced pressure to give a brown gum, 0.487 g. The gum was fractionated by preparative thick layer chromatography (silica, ethyl acetate) to give 8-benzyl-exo-3-(5-chloropyrid-3-yl)-8-azabicyclo[3.2.1]octan-6-one, orange gum, 0.165 g.

$^1$H NMR (CDCl$_3$): δ 1.70–1.90(1H,m); 1.95–2.25(4H,m); 2.80(1H,dd); 2.90–3.10(1H,m); 3.20(1H,broad m); 3.70(1H, broad m); 3.65–3.85(2H,q); 7.25–7.40(5H,m); 7.60(1H,t); 8.35(1H,d); 8.45(1H,d)ppm.

Stage 4

Potassium tert-butoxide (0.062 g) and sodium ethoxide (0.050 g) were dissolved in 1,2-dimethoxyethane (dry, 2 ml) with stirring under an atmosphere of nitrogen and heated to 40° C. The product from Stage 3 (0.150 g) and 4-tolyl methylsulfonylisocyanide (0.134 g) in 1,2-dimethoxyethane (dry, 3 ml) were added and the reaction kept at 40° C. for 6 hours. The mixture was allowed to cool to ambient temperature, stored for 48 hours, poured into water and extracted with ethyl acetate (three times). The combined organic fraction was dried (magnesium sulfate) and evaporated under reduced pressure to give a gum. The gum was fractionated by preparative thick layer chromatography (silica, hexane/ethyl acetate 1:1 by volume) to give the required product, 0.020 g, as a 1:1 mixture of 6-endo-cyano and 6-exo-cyano isomers. Molecular ion 337.

EXAMPLE 27

This Example illustrates the preparation of 8-benzyl-exo-3-(5-chloropyridyl)-8-azabicyclo[3.2.1]oct-6-ene (Compound No. 115 Table II).

Stage 1

8-Benzyl-exo-3-(5-chloropyrid-3-yl)-exo-6-hydroxy-8-azabicyclo[3.2.1]octane (0.500 g) was dissolved with stirring in dichloromethane (dry, 5 ml) containing triethylamine (dry,0.34 ml) and cooled to 0° C. under an atmosphere of nitrogen. Methane sulfonyl chloride (0.14 ml) was added slowly and the reaction mixture was stirred for 30 minutes at 0° C. The mixture was quenched with aqueous sodium carbonate, extracted with dichloromethane (three times) and the combined organic phase dried (magnesium sulfate) then evaporated under reduced pressure to give 8-benzyl-exo-3-(5-chloropyrid-3-yl)-3-endo-cyano-6-exo-methanesulfonyloxy-8-azabicyclo[3.2.1]octane, 0.600 g, as a yellow gum.

$^1$H NMR (CDCl$_3$): δ 1.50–1.70(1H,m); 1.80–1.95(3H,m); 2.35(1H,m); 2.50(1H,m); 2.60–2.80(1H,m); 3.05(3H,s); 3.60(2H,broad m); 3.90(2H,q); 5.30(1H,m); 7.20–7.40 (5H, m); 7.55(1H,t); 8.35(1H,d); 8.45(1H,d)ppm.

Stage 2

The product from Stage 1 (0.200 g) in N-methylpyrrolidin-2-one (dry, 5 ml) containing 18-crown-6 ether (0.005 g, catalyst) and caesium fluoride (0.374 g) were stirred under an atmosphere of nitrogen at 160° C. for 7 hours. The mixture was cooled to ambient temperature, poured into water and extracted into diethyl ether (three times). The combined organic phase was washed with water, dried (magnesium sulfate) and evaporated under reduced pressure to give a yellow oil. The oil was fractionated by preparative thick layer chromatography (silica, 50% ethyl acetate hexane) to give 8-benzyl-exo-3-(5-chloropyridyl)-8-azabicyclo[3.2.1]oct-6-ene as a colourless solid, 0.023 g, mp 101–103° C.

$^1$H NMR (CDCl$_3$): δ 1.65(2H,m); 1.85(2H,m); 2.80–3.00 (1H,m); 3.55(2H,s); 3.60(2H,broad m); 6.05(2H,s); 7.20–7.40(5H,m); 7.60(1H,t); 8.35(1H,d); 8.40(1H,d)ppm.

EXAMPLE 28

This Example illustrates an emulsifiable concentrate composition which is readily convertible by dilution with water into a liquid preparation suitable for spraying purposes. The concentrate has the following composition:

|  | % Weight |
|---|---|
| Compound No. 1 | 25.5 |
| SYNPERONIC NP13 | 2.5 |
| Calcium dodecylbenzenenesulphonate | 2.5 |
| AROMASOL H | 70 |

EXAMPLE 29

This Example illustrates a wettable powder composition which is readily convertible by dilution with water into a liquid preparation suitable for spraying purposes. The wettable powder has the following composition:

|  | % Weight |
|---|---|
| Compound No. 13 | 25.0 |
| Silica | 25.0 |
| Sodium lignosulphonate | 5.0 |
| Sodium lauryl sulphate | 2.0 |
| Kaolinite | 43.0 |

EXAMPLE 30

This Example illustrates a dusting powder which may be applied directly to plants or other surfaces and comprises 1% by weight of Compound No. 25 and 99% by weight of talc.

EXAMPLE 31

This Example illustrates a concentrated liquid formulation suitable for application by ultra low volume techniques after mixing with paraffinic diluents.

|  | % Weight |
|---|---|
| Compound No. 29 | 90.0 |
| SOLVESSO 200 | 10.0 |

EXAMPLE 32

This Example illustrates a capsule suspension concentrate which is readily convertible by dilution with water to form a preparation suitable for application as an aqueous spray.

|  | % Weight |
|---|---|
| Compound No. 43 | 10.0 |
| Alkylbenzene solvent (e.g. AROMASOL H) | 5.0 |
| Toluene di-isocyanate | 3.0 |
| Ethylenediamine | 2.0 |
| Polyvinyl alcohol | 2.0 |
| Bentonite | 1.5 |
| Polysaccharide (e.g. KELTROL) | 0.1 |
| Water | 76.4 |

EXAMPLE 33

A ready for use granular formulation:

|  | % Weight |
|---|---|
| Compound No. 4 | 0.5 |
| SOLVESSO 200 | 0.2 |
| nonylphenol ethoxylate (eg Synperonic NP8) | 0.1 |
| Calcium carbonate granules (0.3–0.7 mm) | 99.2 |

EXAMPLE 34

An aqueous suspension concentrate:

|  | % Weight |
|---|---|
| Compound No. 8 | 5.0 |
| Kaolinite | 15.0 |
| Sodium lignosulphonate | 3.0 |
| nonylphenolethoxylate (eg Synperonic NP 8) | 1.5 |
| propylene glycol | 10.0 |
| Bentonite | 2.0 |
| Polysaccharide (eg Keltrol) | 0.1 |
| Bactericide (eg Proxel; Proxel is a registered Trade Mark) | 0.1 |
| Water | 63.3 |

EXAMPLE 35

This Example illustrates a water dispersible granule formulation.

|  | % Weight |
|---|---|
| Compound No. 20 | 5 |
| Silica | 5 |
| Sodium lignosulphate | 10 |

-continued

| | % Weight |
|---|---|
| Sodium dioctylsulphosuccinate | 5 |
| Sodium acetate | 10 |
| Montmorillonite powder | 65 |

EXAMPLE 36

This Example illustrates the insecticidal properties of the compounds of formula (I). The activity of the compounds of formula (I) was determined using a variety of pests. The pests were treated with a liquid composition containing 500 parts per million (ppm) by weight of the compound unless otherwise stated. The compositions were made by dissolving the compound in acetone and ethanol (50:50) mixture and diluting the solutions with water containing 0.05% by weight of a wetting agent sold under the trade name "SYN-PERONIC" NP8 until the liquid composition contained the required concentration of the compound. "SYNPERONIC" is a Registered Trade Mark.

The test procedure adopted with regard to each pest was basically the same and comprised supporting a number of the pests on a medium which was usually a substrate, a host plant or a foodstuff on which the pests feed, and treating either or both the medium and the pests with the compositions. The mortality of the pests was then assessed at periods usually varying from two to five days after the treatment.

The results of the tests against peach aphid (*Myzus persicae*) are presented below. The results indicate a grading of mortality (score) designated as A, B or C wherein C indicates less than 40% mortality, B indicates 40–79% mortality and A indicates 80–100% mortality; "-" indicates that either the compound was not tested or no meaningful result was obtained. In this test Chinese cabbage leaves were infested with aphids, the infested leaves were sprayed with the test composition, and the mortality assessed after 3 days. Compound Nos. 1–15, 17–20, 22, 26, 28, 30 and 31 of Table I and Compound Nos. 1, 2, 3, 5, 7–14, 16, 17, 19, 23 and 116 of Table II gave a mortality score of A; while Compound Nos. 4, 5 and 7–10 of Table III gave a mortality score of A or B.

In addition, in a similar test against red spider mites (*Tetranychus urticae*) Compounds Nos. 19, 20, 21, 23, 24 and 25 of Table I gave a mortality score of A or B.

The formula referred to hereinabove are set out as follows

(I)

(II)

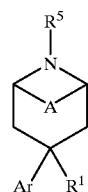

(III)

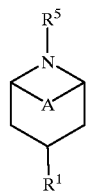

(IV)

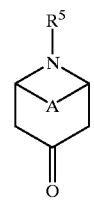

(V)

(VI)

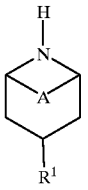

(VII)

-continued

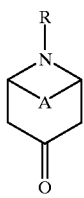
(VIII)

What is claimed is:

1. A compound of formula (I):

(I)

wherein A is a CH=CH; Ar is an optionally substituted phenyl, wherein the substutuents, if present, are selected frog halogen atoms, cyano, alkyl, alkenyl, alkynyl, alkoxy, haloalkyl, haloalkenyl, alkylthio and alkyl amino groups, any of which groups except said cyano group contain up to six carbon atoms; R is hydrogen or cyano or a group selected from alkyl, aryl, heteroaryl, aralkyl, heteroarylalkyl, alkenyl, aralkenyl, alkynyl, alkoxycarbonyl, alkanesulfonyl, arenesulfonyl, alkenyloxycarbonyl, aralkyloxycaxbonyl, aryloxycarbonyl, hetemocyclylalkyl, carbamyl, dithiocarboxyl or $X''R^3$ (where $X''$ represents oxygen or a group $NR^4$), provided that when R is alkenyl, aralkenyl or alkynyl said group does not have an unsaturated carbon atom bonding directly to the ring nitrogen of formula (I); $R^1$ is hydrogen, cyano, hydroxy, alkyl, alkoxy, amino, nitro, isocyanato, acylamino, hydroxyalkyl, optionally substituted heteroaryl, alkoxyalkyl, haloalkyl, halohydroxyalkyl, aralkyloxyalkyl, acyloxyalkyl, amidoximido, sulfonyloxyalkyl, aminoalkyl, alkoxycarbonylamino, acylaminoalkyl, cyanoalkyl, imino, formyl, acyl or carboxylic acid or an ester or amide thereof, or alkenyl or alkynyl either of which is optionally substituted by halogen, alkoxy, cycloalkyl, optionally substituted aryl, optionally substituted heteroaryl or cyano; $R^3$ and $R^4$ are, independently, hydrogen, alkyl, aryl, heteroaryl, aralkyl, heteroarylalkyl, alkenyl, aralkenyl, alkynyl, heterocyclylalkyl, alkoxycarbonyl or carboxylic acyl; alkyl moieties of R, $R^3$ and $R^4$ comprise from 1 to 15 carbon atoms, and are optionally substituted with one or more substituents selected from, halogen, cyano, carboxyl, carboxylic acyl, carbamyl, alkoxycarbonyl, alkoxy, alkylenedioxy, hydroxy, nitro, amino, acylamino, imidate and phosphonato groups; aryl, heteroaryl, aralkyl, heteroarylalkyl, alkenyl, aralkenyl, alkynyl, alkoxycarbonyl, alkanesulfonyl, arenesulfonyl, alkanyloxycarbonyl, aralkyloxycarbonyl, aryloxycarbonyl, heterocyclylalkyl, carbamyl, dithiocarboxyl moieties of R, $R^3$ and $R^4$ comprise from 1 to 15 carbon atoms, and are optionally substituted with one or more substituents selected from, halogen, cyano, carboxyl, carboxylic acyl, carbamyl, alkoxycarbonyl, alkoxy, alkylenedioxy, hydroxy, nitro, haloalkyl, alkyl, amino, acylamino, imidate and phosphonato groups; or an acid addition salt, quaternary ammonium salt or N-oxide derived therefrom.

2. A compound of formula (I) as claimed in claim 1 wherein $R^1$ is cyano.

3. A compound of formula (I) as claimed in claim 1 wherein R is $C_{1-4}$ alkyl (optionally substituted with cyano, $CO_2(C_{1-4}$ alkyl) or phenyl (optionally substituted with halogen, $C_{1-4}$ alkyl, $C_{1-4}$ alkoxy, $C_{1-4}$ haloalkyl or $C_{1-4}$ haloalkoxy)), $C_{2-4}$ haloalkyl (the α-carbon being unsubstituted), $C_{3-4}$ alkenyl or $C_{3-4}$ alkynyl; provided that when R is alkenyl or alkynyl said group does not have an unsaturated carbon atom bonding directly to the ring nitrogen of formula (I).

4. A compound of formula (I) as claimed in claim 1 wherein Ar is a substituted phenyl, wherein the substituents are selected from halogen, $C_{1-4}$ alkyl, $C_{1-4}$ alkoxy, $C_{2-4}$ alkenyl, $C_{2-4}$ alkynyl or cyano.

5. An insecticidal, acaricidal or nematicidal composition comprising an insecticidally, acaricidally or nematicidally effective amount of a compound of formula (I) as claimed in claim 1 and a suitable carrier or diluent therefor.

6. A method of combating and controlling insect, acarine or nematode pests at a locus which comprises treating the pests or the locus of the pests with a pesticidally effective amount of a compound according to claim 1.

7. A method of combating and controlling insect, acarine, or nematode pests at a locus which comprises treating the pests or the locus of the pests with a pesticidally effective amount of the composition of claim 5.

8. A method according to claim 6 wherein the pests are insect pests of growing plants.

9. A method according to claim 7 wherein the pests are insect pests of growing plants.

* * * * *